US010729314B2

(12) United States Patent
Kudo

(10) Patent No.: US 10,729,314 B2
(45) Date of Patent: Aug. 4, 2020

(54) HOLDING MECHANISM AND INSERTION DEVICE

(71) Applicant: OLYMPUS CORPORATION, Tokyo (JP)

(72) Inventor: Ryota Kudo, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 595 days.

(21) Appl. No.: 15/439,114

(22) Filed: Feb. 22, 2017

(65) Prior Publication Data

US 2017/0156576 A1    Jun. 8, 2017

Related U.S. Application Data

(63) Continuation of application No. PCT/JP2015/075207, filed on Sep. 4, 2015.

(30) Foreign Application Priority Data

Oct. 17, 2014  (JP) .................................. 2014-212823

(51) Int. Cl.
*A61B 1/00*         (2006.01)
*A61B 1/018*        (2006.01)
(Continued)

(52) U.S. Cl.
CPC .............. *A61B 1/018* (2013.01); *A61B 1/005* (2013.01); *A61B 1/00131* (2013.01);
(Continued)

(58) Field of Classification Search
CPC ....... A61B 1/018; A61B 1/0125; A61B 1/012; A61B 1/00131; A61B 1/00133;
(Continued)

(56) References Cited

U.S. PATENT DOCUMENTS 6,096,009 A * 8/2000 Windheuser ...... A61M 25/0097
24/339
6,893,393 B2 * 5/2005 Carrillo ................. A61M 25/02
600/104
(Continued)

FOREIGN PATENT DOCUMENTS

JP    2008-529723 A    8/2008
JP    2009-538691 A    11/2009

OTHER PUBLICATIONS

International Search Report dated Dec. 1, 2015 issued in PCT/JP2015/075207.
(Continued)

*Primary Examiner* — Anh Tuan T Nguyen
*Assistant Examiner* — Pamela F Wu
(74) *Attorney, Agent, or Firm* — Scully, Scott, Murphy & Presser, P.C.

(57) ABSTRACT

A holding mechanism includes a first guide portion which contacts and guides part of a guide member in a state where the guide member exposed from an insertion opening portion of the insertion device is bent, and a second guide portion which permits passage of the part of the guide member which has been guided by the first guide portion. The holding mechanism also includes a regulating/fixing portion which is arranged parallel to a flat face where an insertion opening portion is provided, which is continuous with the second guide portion, and which positions and fixes the part such that the guide member including the part having passed the second guide portion maintains a bent state with respect to the insertion opening portion.

19 Claims, 11 Drawing Sheets

(51) Int. Cl.
*A61B 1/005* (2006.01)
*G02B 23/24* (2006.01)

(52) U.S. Cl.
CPC ...... *A61B 1/00133* (2013.01); *A61B 1/00137* (2013.01); *A61B 1/0014* (2013.01); *G02B 23/2476* (2013.01)

(58) Field of Classification Search
CPC ....... A61B 1/0014; A61B 1/0112; A61B 1/04; A61B 1/00098; A61B 1/00137; A61B 1/00066; A61B 1/00068; A61B 1/005; A61B 1/00147; A61B 1/01; A61M 25/0169; A61M 25/0172; A61M 2025/0177; A61M 2025/018; A61M 2025/0183; A61M 2025/0186
USPC ................................ 600/104, 106, 153, 131
See application file for complete search history.

(56) References Cited

U.S. PATENT DOCUMENTS

2006/0195117 A1* 8/2006 Rucker .............. A61B 1/00137
606/108
2007/0282166 A1 12/2007 Ayala et al.
2010/0081878 A1* 4/2010 Byers ................. A61B 1/00137
600/125

OTHER PUBLICATIONS

English translation of International Preliminary Report on Patentability dated Apr. 27, 2017 together with the Written Opinion received in related International Application No. PCT/JP2015/075207.

* cited by examiner

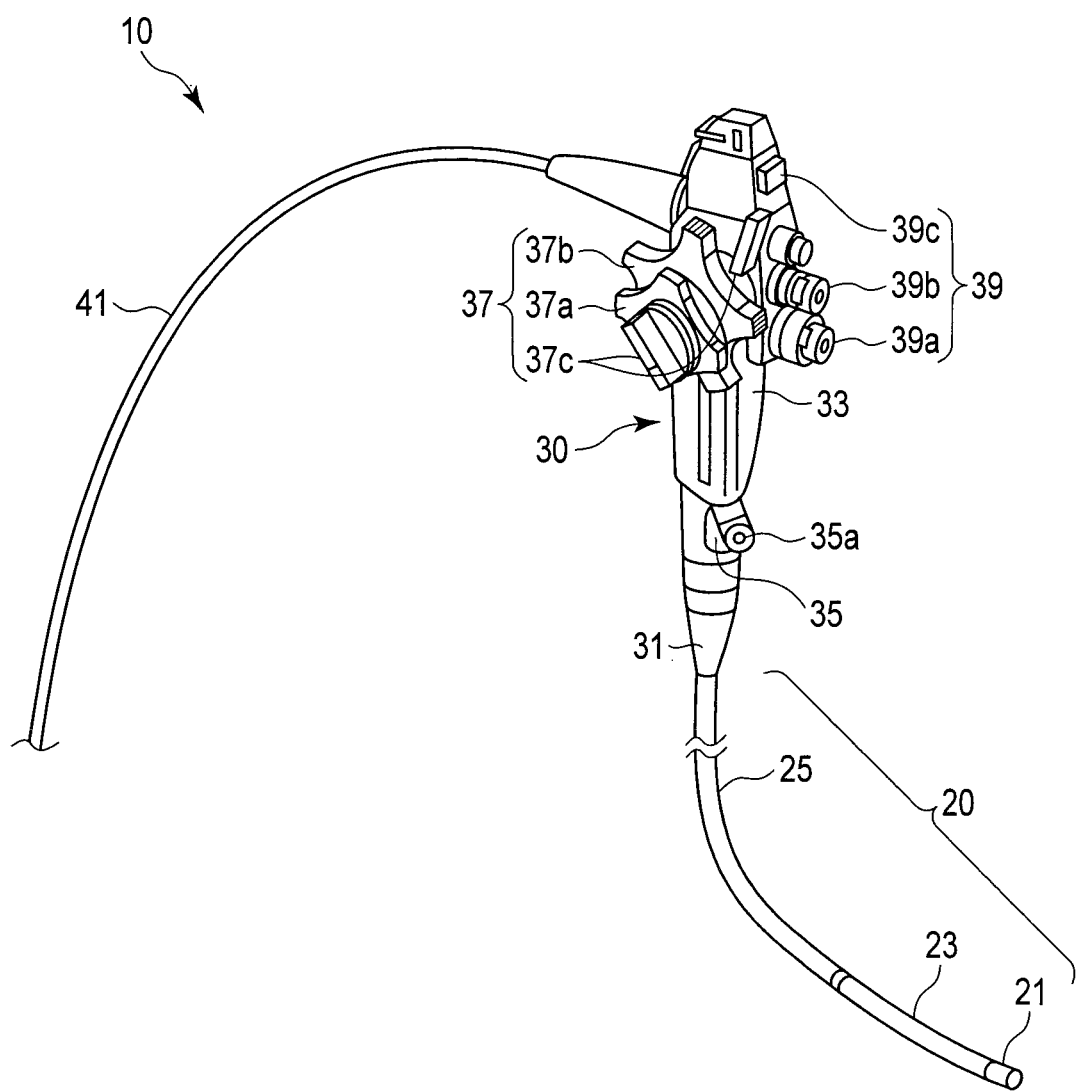
F I G. 1A

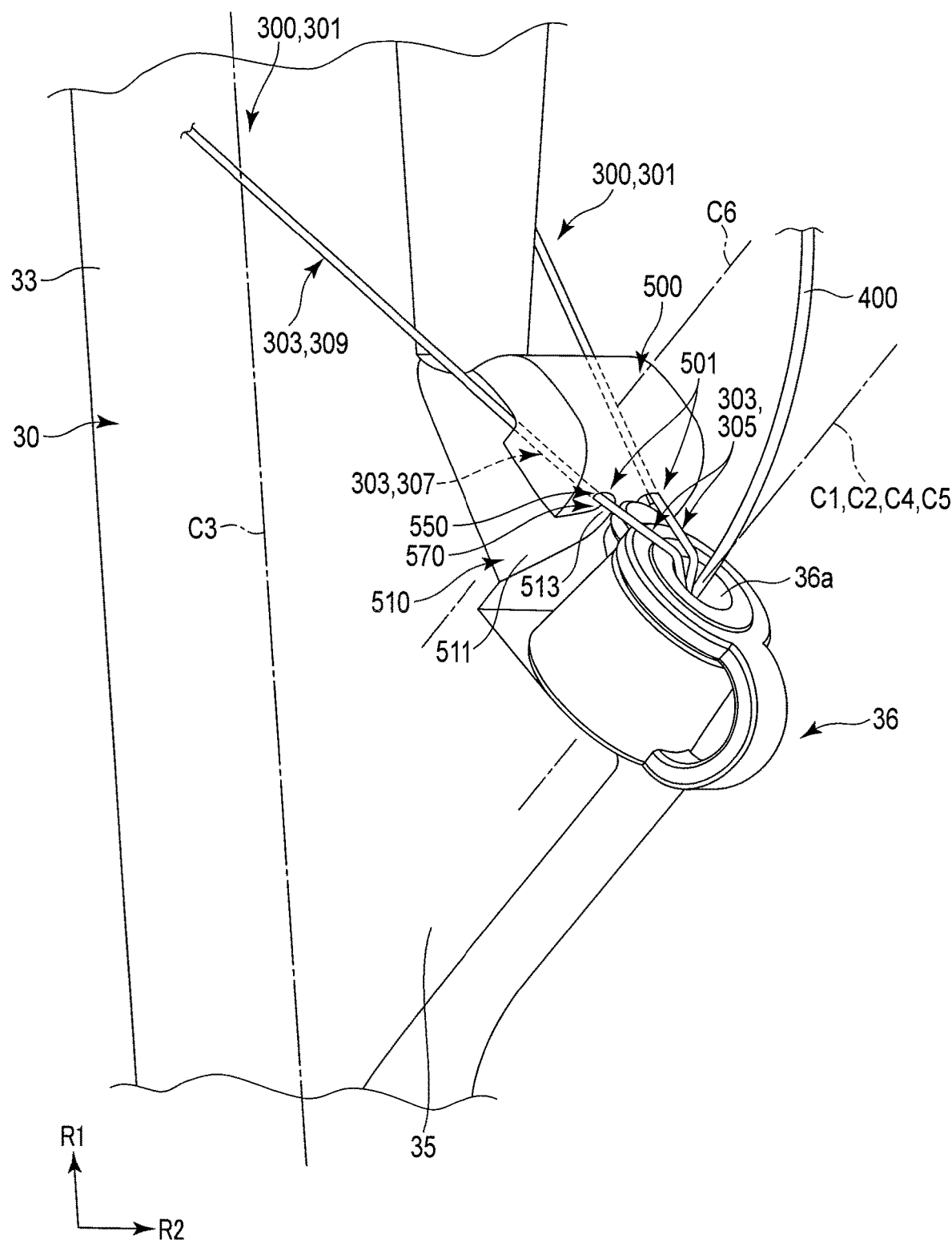
F I G. 1B

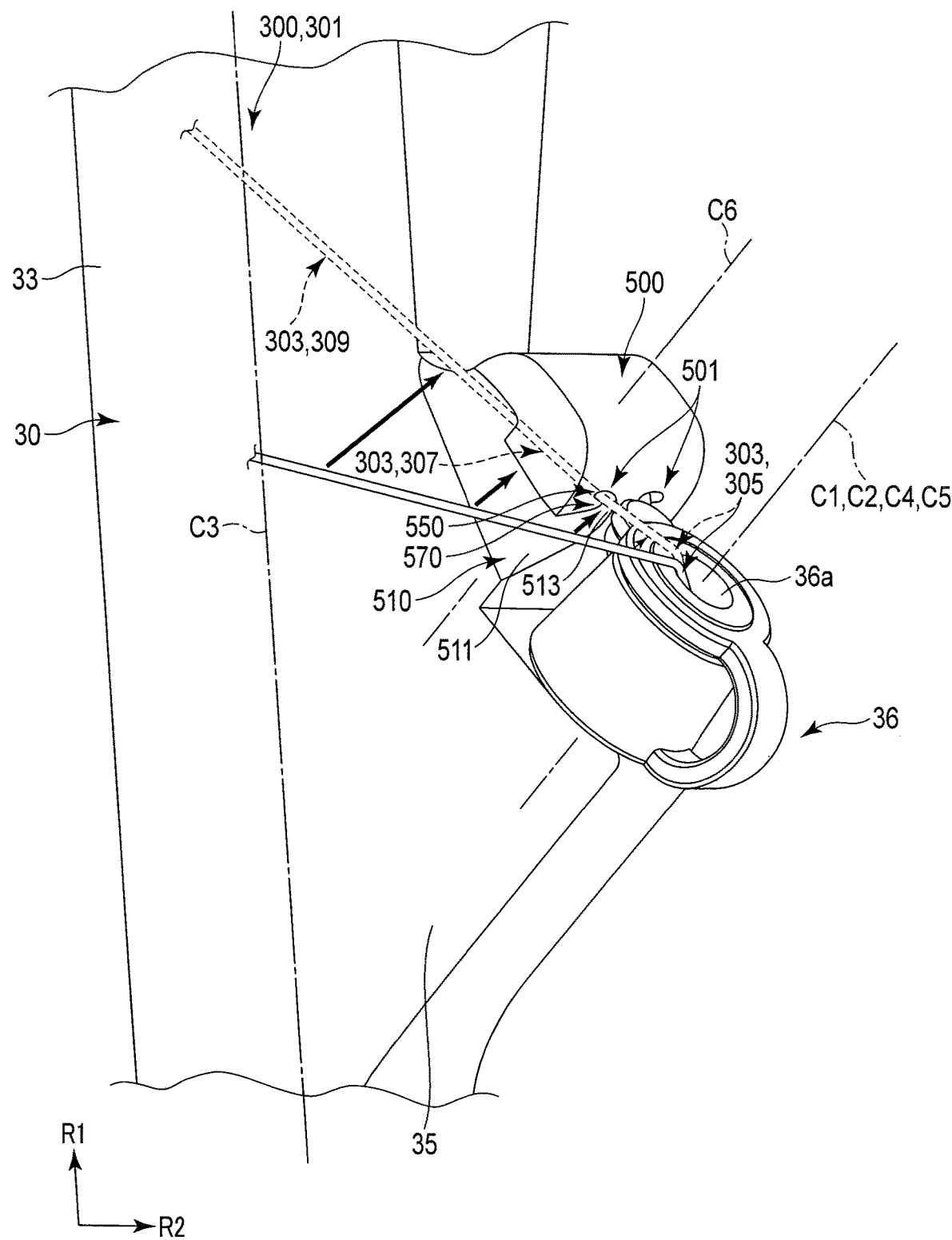
F I G. 3A

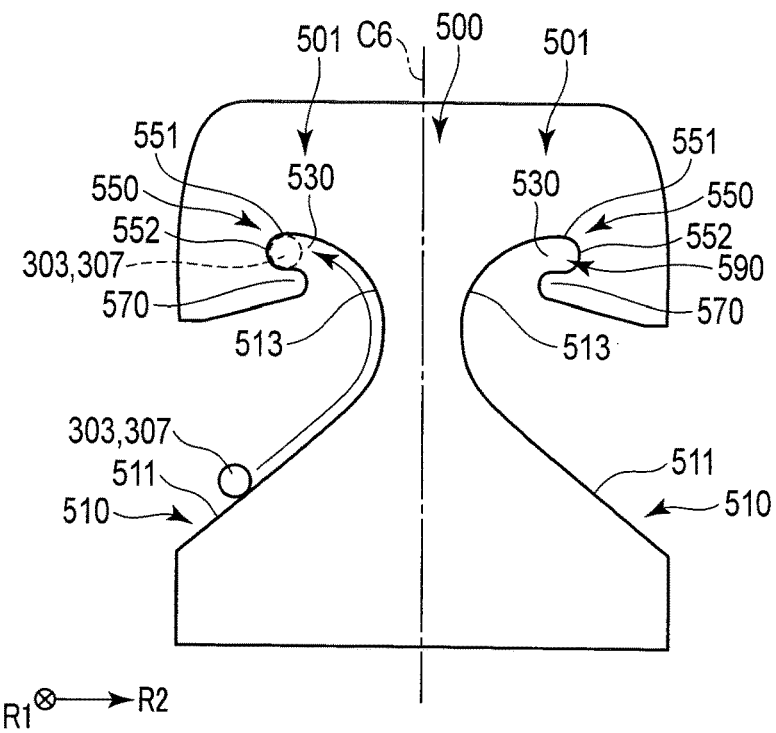
F I G. 3B
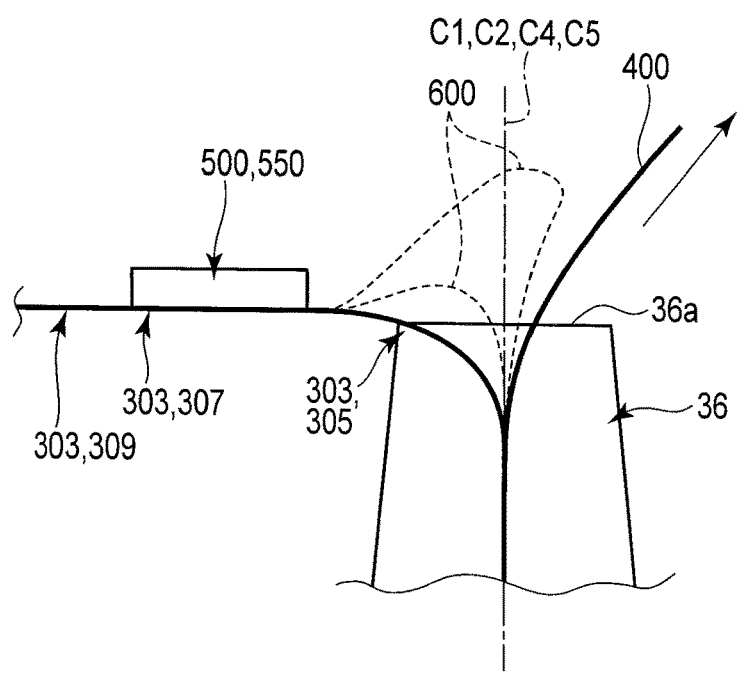
F I G. 4A

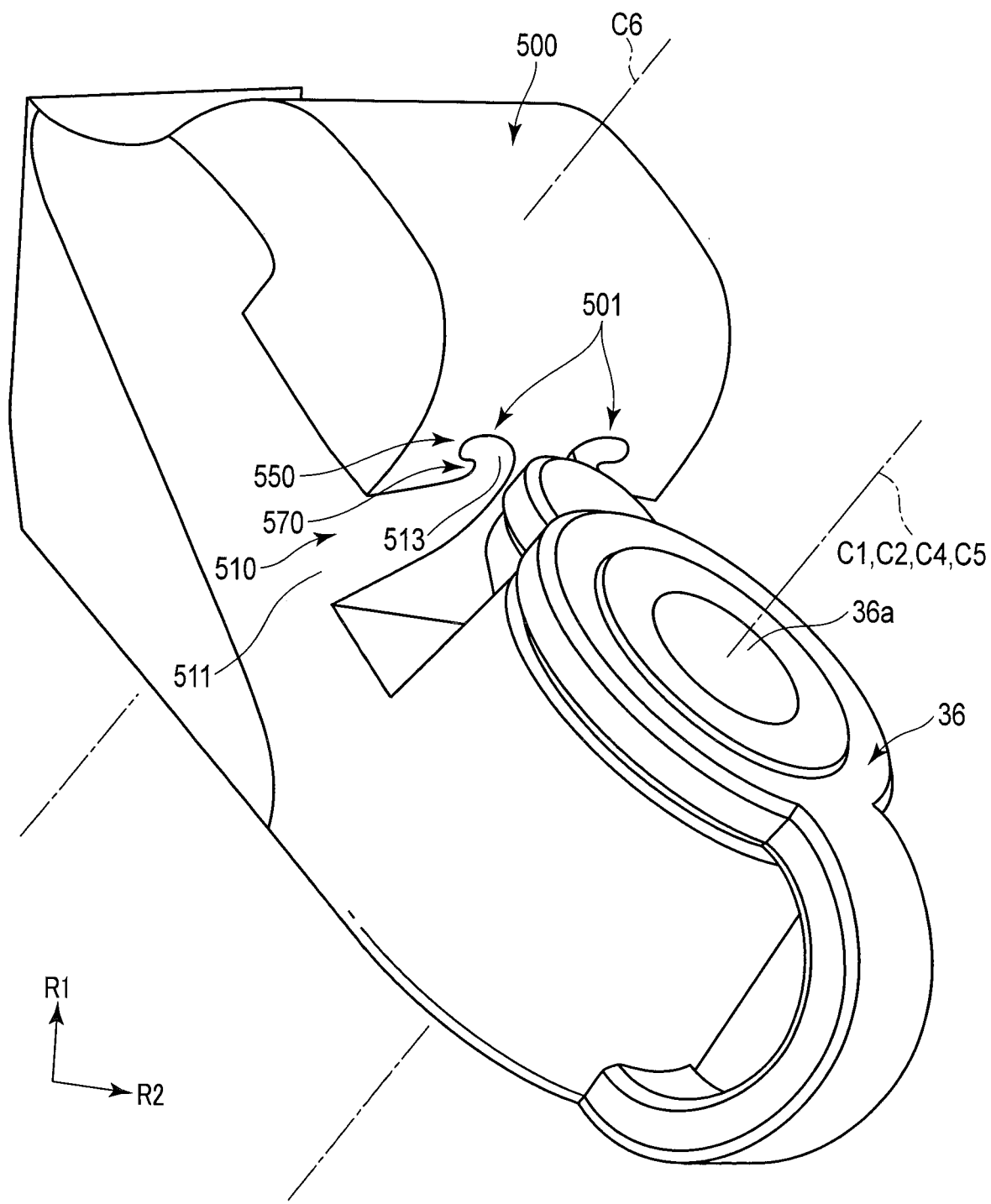
F I G. 5A

HOLDING MECHANISM AND INSERTION DEVICE

CROSS-REFERENCE TO RELATED APPLICATION

This application is a Continuation Application of PCT Application No. PCT/JP2015/075207, filed Sep. 4, 2015 and based upon and claiming the benefit of priority from prior Japanese Patent Application No. 2014-212823, filed Oct. 17, 2014, the entire contents of all of which are incorporated herein by reference.

BACKGROUND OF THE INVENTION

1. Field of the Invention

The present invention relates to a holding mechanism which holds a guide member to guide a treatment tool to a subject, and to an insertion device having such a holding mechanism.

2. Description of the Related Art

For example, Jpn. Pat. Appln. KOKAI Publication No. 2008-529723 discloses a holding member which holds a guide member guiding a treatment tool to a subject. When the holding member holds the guide member, the guide member is positioned and fixed, and the guide member is prevented from being shifted from the right position. The holding member is a separate member from an endoscope and is removably attached to a treatment tool insertion portion of the endoscope.

BRIEF SUMMARY OF THE INVENTION

According to one aspect of the invention, a holding mechanism holds a guide member used for guiding a treatment tool which is inserted into a cavity by way of the insertion portion of an insertion device inserted into the cavity. The holding mechanism comprises: a first guide portion which contacts and guides part of the guide member in a state where the guide member exposed from an insertion opening portion of the insertion device is bent; a second guide portion which permits passage of the part guided by the first guide portion; and a regulating/fixing portion which is arranged parallel to a flat face where the insertion opening portion is provided, which is continuous with the second guide portion, and which positions and fixes the part such that the guide member including the part having passed the second guide portion maintains a bent state with respect to the insertion opening portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a perspective view of an insertion device according to one embodiment of the present invention.

FIG. 1B is a perspective view of a holding mechanism which holds a guide member and of structural elements around the holding mechanism.

FIG. 3A is a perspective view illustrating how a guide operation and a positioning/fixing operation are performed.

FIG. 3B is a front view illustrating how the guide operation and the positioning/fixing operation are performed.

FIG. 4A illustrates how a bent/pressed part is prevented from being deformed when a replacement operation is performed.

FIG. 5A is a perspective view showing how a holding mechanism provided in a forceps plug portion is modified.

DETAILED DESCRIPTION OF THE INVENTION

Hereinafter, embodiments of the present invention will be described with reference to the accompanying drawings.

First Embodiment

[Configuration]

Figure 1C:
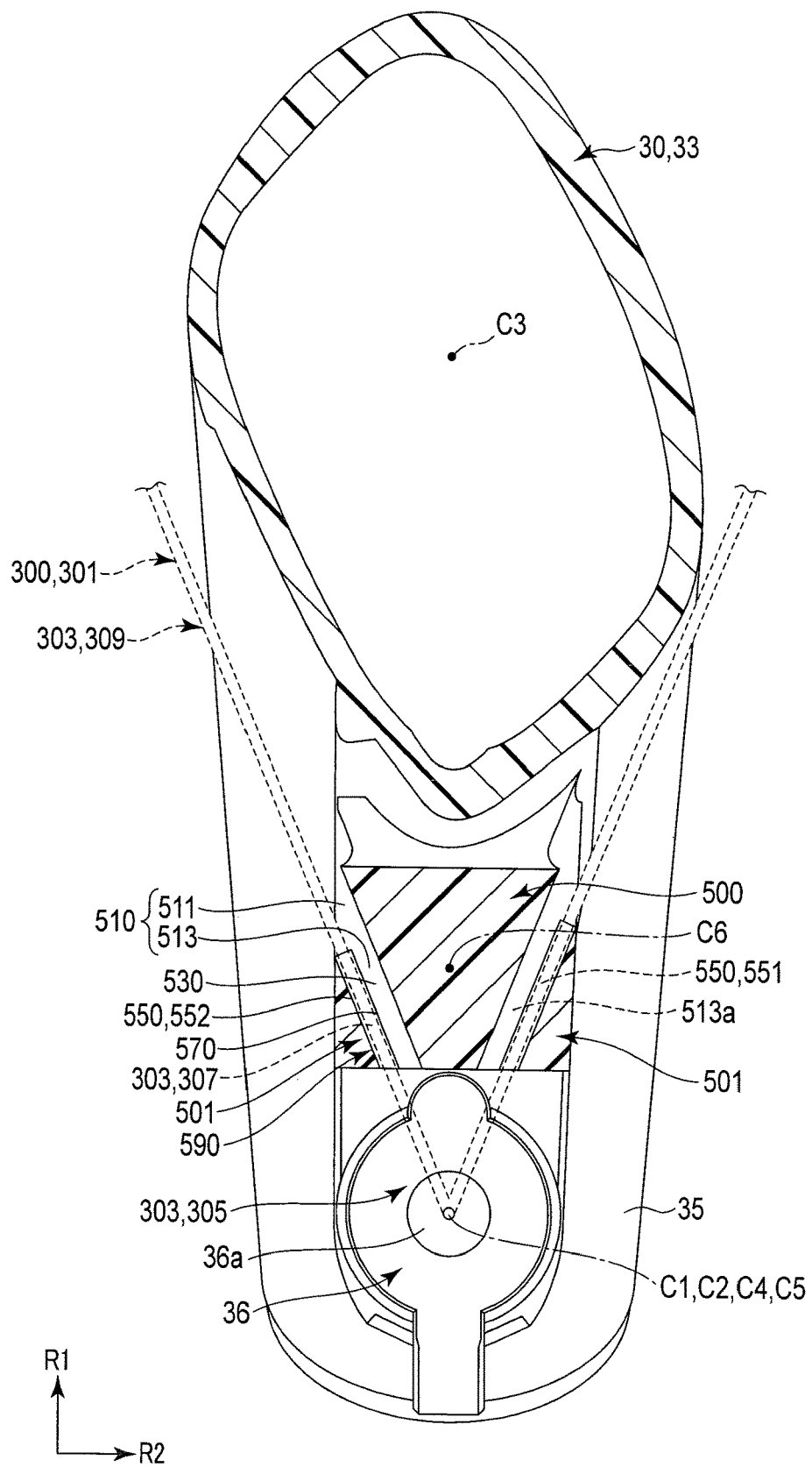
FIG. 1C is a transverse cross section of the holding mechanism.

An embodiment will be described with reference to FIGS. 1A, 1B, 1C, 2A, 2B, 2C, 2D, 3A, 3B, 4A, 4B and 4C. In some of the Figures, illustration of some structural elements is omitted for the sake of easy understanding of the structure. For example, in FIG. 1A, illustration of a forceps plug portion 36 and a holding mechanism 500 is omitted.

[Insertion Device 10]

An insertion device 10 such as that shown in FIG. 1A functions as an endoscope which is to be inserted into a lumen inside a body cavity. The insertion device 10 of the present embodiment is a side-viewing type endoscope which permits a treatment tool 400 to be inserted to a duodenal papilla or a biliary and pancreatic area. The insertion device 10 of the present embodiment may be a direct-viewing type endoscope, or may be an endoscope which permits a treatment tool 400 to be inserted to body portions different from those mentioned above.

A description will be given of the case where the insertion device 10 of the embodiment is a medical endoscope though this does not restrict the invention. The insertion device 10 may be suitably realized not only as the medical endoscope but also as an industrial endoscope or as an insertion device having neither illumination optical system nor observation optical system (e.g., a catheter).

As shown in FIG. 1A, the insertion device 10 comprises an elongated hollow insertion portion 20 to be inserted into the lumen, and an operation portion 30 coupled to a proximal end portion of the insertion portion 20 and configured to operate the insertion portion 10.

[Insertion Portion 20]

As shown in FIG. 1, the insertion portion 20 includes, from its distal end portion to its proximal end portion, a distal hard portion 21, a bendable portion 23 and a flexible tube portion 25. A proximal end portion of the distal hard portion 21 is coupled to a distal end portion of the bendable portion 23, and a proximal end portion of the bendable portion 23 is coupled to a distal end portion of the flexible tube portion 25.

The distal hard portion is the distal end portion of the insertion portion 20, is hard and cannot be bent. Where the insertion device 10 is a side-viewing type endoscope, the distal hard portion 21 has a known structure (not shown). That is, the distal hard portion 21 includes a distal opening portion arranged on a side surface thereof, and a treatment tool raising table received in the distal opening portion and remotely swingable in response to a raising operation performed on a hand side. The treatment tool raising table is swingable between a received position where it is laid to a body portion of the distal hard portion 21 and is received in the distal hard portion 21 and a raised position where it is projected (raised) from the distal opening portion. The treatment tool raising table is swung in accordance with a raising operation and causes a treatment tool 400 to come out of the distal opening portion and to be projected on the side of the distal hard portion 21. The distal hard portion 21 includes an air/water supply nozzle, an imaging unit and an illumination unit.

The bendable portion 23 can be bent in any direction desired (e.g., in the upward/downward direction and rightward/leftward direction) in response to the operation of a bending operation portion 37 mentioned later. The position and direction of the distal hard portion 21 are changed by the bending operation of the bendable portion 23. Illumination light (not shown) is radiated to an observation target, and the observation target is caught within an observation field. The observation target is, for example, an affected portion or a disease portion of a subject (e.g., a portion of the body cavity).

The flexible tube portion 25 has desirable flexibility. The flexible tube portion 25 can be bent by an external force. The flexible tube portion 25 is a tubular member extended from a body portion 31 (described later) of the operation portion 30.

[Operation Portion 30]

As shown in FIG. 1A, the operation portion 30 includes a body portion 31 from which the flexible tube portion 25 extends, a grasp portion 33 coupled to a proximal end portion of the body portion 31 and held by an operator who operates the insertion device 10, and a universal cord 41 connected to the grasp portion 33.

[Grasp Portion 33]

As shown in FIG. 1A, the grasp portion 33 includes a treatment tool insert portion 35, a bending operation portion 37 which is operated to bend a bendable portion 23, and a switch portion 39. The treatment tool insertion portion 35 is located on a distal end portion side of the grasp portion 33, while the bending operation portion 37 and the switch portion 33 are located on a proximal end portion side of the grasp portion 33.

[Treatment Tool Insertion Portion 35]

As shown in FIG. 1A, the treatment tool insertion portion 35 is a portion branching from the grasp portion 33. That is, a direction of a central axis C2 of the treatment tool insertion portion 35 is slanted with reference to a direction of a central axis C3 of the grasp portion 33.

As shown in FIG. 1A, the treatment tool insertion portion 35 has a treatment tool insertion opening portion 35a at an end portion thereof. From this treatment tool insertion opening portion 35a, a guide member 300 and a treatment tool 400, which will be described later, are inserted.

The treatment tool insertion opening portion 35a is coupled to the proximal end portion of a treatment tool insertion channel (not shown). The treatment tool insertion channel is arranged inside the insertion portion 20 and extends from the flexible tube portion 25 to the distal hard portion 21 through the bendable portion 23. The distal end portion of the treatment tool insertion channel communicates with a distal end opening portion arranged in the distal hard portion 21. The treatment tool insertion opening portion 35a defines an insertion port from which the guide member 300 and the treatment tool 400 are inserted into the treatment tool insertion channel.

As shown in FIG. 1A, a central axis C1 of the treatment tool insertion portion 35a is coaxial with the central axis C2 of the treatment tool insertion portion 35, so that the central axis C1 of the treatment tool insertion opening portion 35a is slanted with reference to the central axis C3 of the grasp portion 33. That is, a direction of the central axis C1 of the treatment tool insertion opening portion 35a is slanted with reference to the direction of the central axis C3 of the grasp portion 33.

As shown in FIG. 1B, the treatment tool insertion portion 35 includes a tubular forceps plug portion 36, which is removably attached to the treatment tool insertion portion 35. The forceps plug portion 36 is formed of a resin material, such as rubber. A central axis C4 of the forceps plug portion 36 is coaxial with the central axis C1 of the treatment tool insertion opening portion 35a. Therefore, the forceps plug portion 36 is slanted with reference to the grasp portion 33. When the forceps plug portion 36 is attached to the treatment tool insertion portion 35, it communicates with the treatment tool insertion channel by way of the treatment tool insertion opening portion 35a. The tubular forceps plug portion 36 has an insertion opening portion 36a from which the guide member 300 and the treatment tool 400 are inserted into the interior of the insertion device 10, namely, into the treatment tool insertion channel. A central axis C5 of the insertion opening portion 36a is coaxial with the central axis C4 of the forceps plug portion 36.

The guide member 300 and treatment tool 400 shown in FIG. 1B are inserted from the insertion opening portion 36a into the treatment tool insertion channel by way of the forceps plug portion 36 and the treatment tool insertion opening portion 35a, and are pushed toward the distal hard portion 21. The guide member 300 and the treatment tool 400 are projected from the distal opening portion.

[Bending Operation Portion 37]

As shown in FIG. 1A, the bending operation portion 37 includes a right/left operation knob 37a for bending the bendable portion 23 rightward or leftward, an up/down operation knob 37b for bending the bendable portion 23 upward or downward, and a fixing knob 37c for fixing the position of the bent bendable portion 23.

[Switch Portion 39]

As shown in FIG. 1A, the switch portion 39 includes a suction switch 39a, an air/water switch 39b and a variety of switches 39c operated for endoscopic imaging. The suction switch 39a, air/water switch 39b and switches 39c are operated by a hand of the operator when the grasp portion 33 is grasped by the operator.

The suction switch 39a is operated when the insertion device 10 sucks a fluid (including mucus) from the distal opening portion (which functions as a suction opening portion as well) by way of the treatment tool insertion channel (which functions as a suction channel as well).

The air/water switch 39b is operated when a gaseous fluid is supplied from an air tube (not shown) and an air/water tube (not shown) and when a liquid fluid is supplied from a water tube and the air/water tube, so as to ensure a field of observation of an imaging unit (not shown) at the distal hard portion 21. The fluid includes water and a gas.

Inside the insertion device 10, the air tube, the water tube and the air/water tube are extended from the insertion portion 20 to the universal cord 41 by way of the body portion 31 and the grasp portion 33.

[Universal Cord 41]

As shown in FIG. 1A, the universal cord 41 extends from a side face of the grasp portion 33.

[Guide Member 300, Treatment Tool 400 and Holding Mechanism 500]

As can be seen in FIG. 1B, the insertion device 10 is used together with the guide member 300 and the treatment tool 400, which are provided independently of the insertion device 10. The insertion device 10 is therefore provided with a holding mechanism 500 for holding the guide member 300. The guide member 300 is inserted from the insertion opening portion 36a into the treatment tool insertion channel by way of the forceps plug portion 36, is projected from the distal opening portion, and reaches the subject. The guide member 300 serves to guide the treatment tool 400 to the subject. The holding mechanism 500 holds the guide member 300 to guide the treatment tool 400 which is inserted into the lumen through the insertion portion 20 of the insertion device 10 that is inserted into the lumen. In the state where the guide member 300 is projected from the distal opening portion arranged at the distal end of the insertion portion 20, the guide member 300 is arranged such that it is movable in the axial direction thereof. With this arrangement, the guide member 300 guides the treatment tool 400.

[Guide Member 300]

As shown in FIG. 1B, the guide member 300 is inserted from the insertion opening portion 36a into the treatment tool insertion channel by way of the forceps plug portion 36 and the treatment tool insertion opening portion 35a. A distal end portion of the guide member 300 is inserted through the treatment tool insertion channel and is projected from the distal opening portion. Since the distal opening portion is arranged on the side face, the distal end portion of the guide member 300 is projected toward a side position of the distal end portion of the insertion portion 20. In this state, the distal end portion of the guide member 300 reaches the subject. In the state where the distal end of the guide member 300 is projected out of the distal opening portion, a proximal end portion 301 of the guide member 300 is projected from the insertion opening portion 36a and is thus exposed an outside of the insertion device 10.

As shown in FIG. 1B, in the exposed proximal end portion 301, a part 303 of the guide member 300 which has appeared from the insertion opening portion 36a to the outside is in a bent state where it is bent from the insertion opening portion 36a toward, for example, the grasp portion 33 of the operation portion 30, and is also in a pressure contact state where it is brought into pressure contact with the forceps plug portion 36 including the insertion opening portion 36a.

For the sake of simplicity, the above-mentioned part of the guide member 300 will be referred to as a bent/pressed part 305. Details of the bent state and details of the pressure contact state will be described later.

Another part indicated by 303 is continuous with the bent/pressed part 305, is adjacent to the bent/pressed part 305, and is held by the holding mechanism 500.

For the sake of simplicity, the above-mentioned part of the guide member 300 will be referred to as a held part 307.

Another part indicated by 303 is continuous with the held part 307, is adjacent to the held part 307, and is extended, for example, to a side region of the grasp portion 33 of the operation section 30.

For the sake of simplicity, the above-mentioned part of the guide member 300 will be referred to as an extension part 309. The extension part 309 is not held by the holding mechanism 500 and is a portion extended from the holding mechanism 500 to an outside of the holding mechanism 500.

As shown in FIG. 1B, the exposed proximal end portion 301 includes a bent/pressed part 305, a held part 307 and an extension part 309. In the proximal end portion 301, the bent/pressed part 305, the held part 307 and the extension part 309 are arranged in the order mentioned, from the distal end portion of the guide member 300 to the proximal end portion thereof. As mentioned above, the bent/pressed part 305, the held part 307 and the extension part 309 are different parts. The extension part 309 is longer than the bent/pressed part 305 and the held part 307.

The guide member 300 is inserted from the insertion opening portion 36a into the treatment tool insertion channel by way of the forceps plug portion 36, simultaneous with the treatment tool 400 or prior to the treatment tool 400, in accordance with a surgical operation. Whether the guide member 300 is inserted simultaneous with the treatment tool 400 or prior to the treatment tool is determined in accordance with the surgical operation to be performed. The guide member 300 guides the treatment tool 400 to the subject.

The guide member 300 is made, for example, of a thin wire member. The wire member includes, for example, a wire of a hard metal having high resilience. Because of the resilience, the guide member 300 is inhibited from having a bending tendency. The "bending tendency" is intended to mean that a member (e.g., the guide member 300) does not return to the original state (e.g., substantially linear state) after it is bent. Because of the resilience, the guide member 300 returns to the original state (e.g., a substantially linear state) even if it is bent. The metal mentioned above includes, for example, at least one of nickel titanium alloy and stainless steel. The wire member may include, for example, a nickel titanium wire and fluororesin coated on the surface of the nickel titanium wire. The guide member 300 is, for example, a disposable type.

[Treatment Tool 400]

The treatment tool 400, such as that shown in FIG. 1B, is used for treating the subject such as a bile duct. This type of treatment tool 400 includes, for example, a knife for endoscopic sphincterotomy (hereinafter referred to as EST). The treatment tool 400 is, for example, a thin wire member.

The treatment tool 400 is guided by the guide member 300 to the subject at timings suitable for the surgical operation.

[Holding Mechanism 500]

In general, the treatment tool 400 is advanced or retreated in a axial direction thereof by an operation of a right hand of the operator in the state the grasp portion 33 is grasped by a left hand of the operator. Therefore, the holding mechanism 500 is provided in the operation portion 30 such that the holding mechanism 500 can be made to hold or release the part 307 by an operation of the right hand of the operator, in the state where the grasp portion 33 is kept grasped by the left hand of the operator. In other words, the holding mechanism 500 is provided in the operation portion 30 such that the part 307 can be attached to or detached from the grasp portion 33 through the holding mechanism 500 by the operation of the right hand of the operator, in the state where the grasp portion 33 is kept grasped by the left hand of the operator. In this manner, the holding mechanism 500 is provided in the operation portion 30 such that the holding mechanism 500 does not become an obstacle to the operation performed by the left hand of the operator who manipulates the insertion device 10 and such that the guide member 300, the treatment tool 400 and the holding mechanism 500 can be operated by the operation the right hand of the operator.

As shown in FIG. 1B, the holding mechanism 500 is provided in the operation portion 30 coupled to the proximal end portion of the insertion portion 20. In this case, the holding mechanism 500 is arranged adjacent to the insertion opening portion 36a (i.e., to the forceps plug portion 36), as shown in FIG. 1B. The holding mechanism 500 is located between the forceps plug portion 36 and the grasp portion 33. Therefore, a central axis C6 of the holding mechanism 500 is offset with respect to the central axis C5 of the insertion opening portion 36a (forceps plug portion 36) such that the central axis C6 of the holding mechanism 500 is located between the central axis C3 of the grasp portion 33 and the central axis C5 of the insertion opening portion 36a (forceps plug portion 36). In other words, the central axis C6 of the holding mechanism 500 is substantially parallel to the central axis C5 of the insertion opening portion 36a.

As shown in FIG. 1B, the holding mechanism 500 is integrally formed, for example, with the grasp portion 33 and treatment tool insertion portion 35 of the operation portion 30. Alternatively, the holding mechanism 500 may be a separate mechanism removable from the operation portion 30 though illustration of this structure is omitted.

Where the holding mechanism 500 is integrally formed with the operation portion 30, it is integral with the side face of the grasp portion 33 and a flat face of the treatment tool insertion portion 35 (on which the forceps plug portion 36 is arranged). The holding mechanism 500 is formed by insert molding, together with the grasp portion 33.

Where the holding mechanism 500 is a separate mechanism made independently of the operation portion 30 (which structure is not shown in the drawings), the holding mechanism 500 is detachably attached to the grasp portion 33 and the treatment tool insertion portion 35. In this case, the holding mechanism 500 may be attached to the grasp portion 33 and the treatment tool insertion portion 35 by adhesion.

Figure 2A:
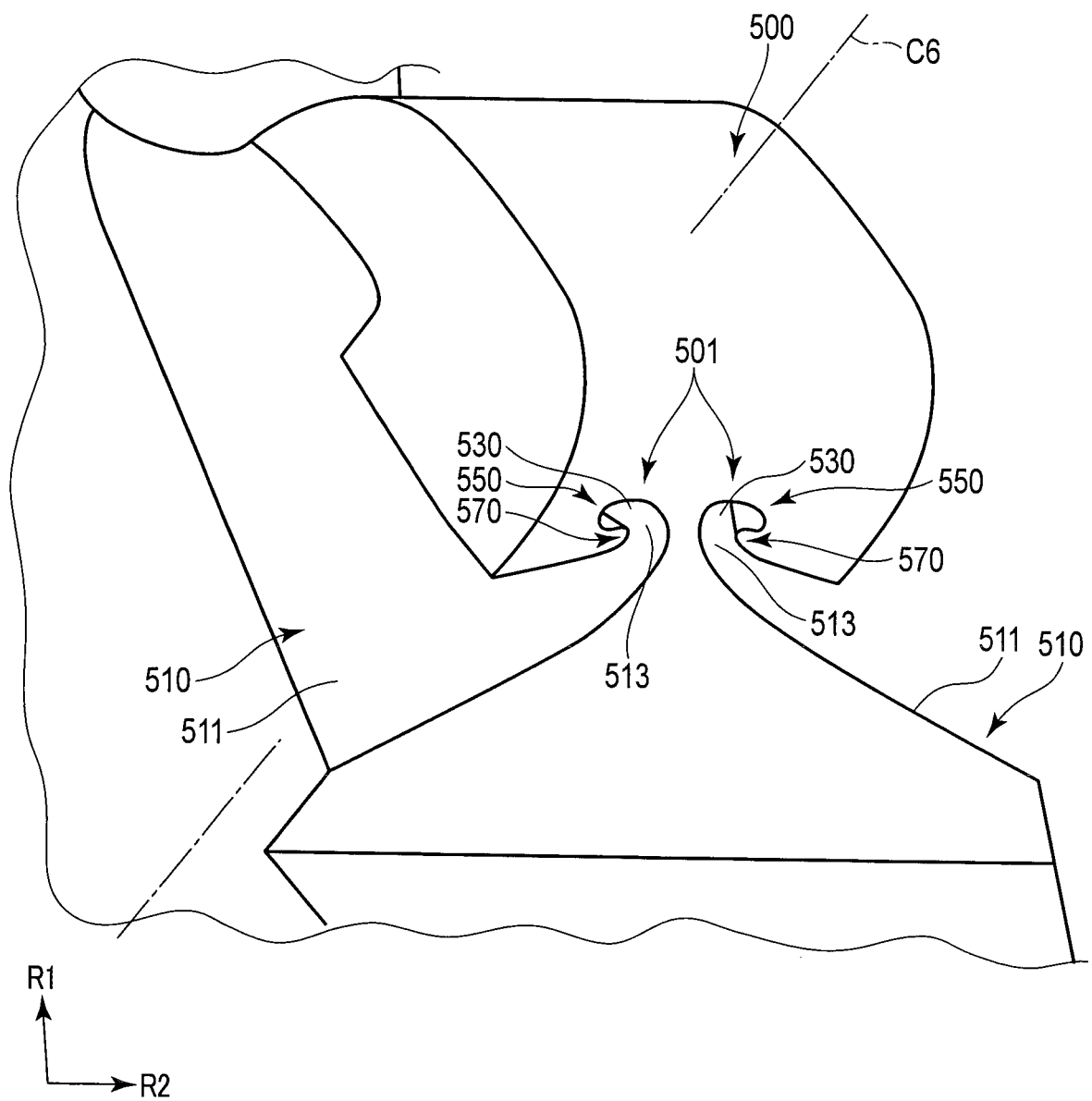
FIG. 2A is a perspective view of the holding mechanism.
Figure 2B:
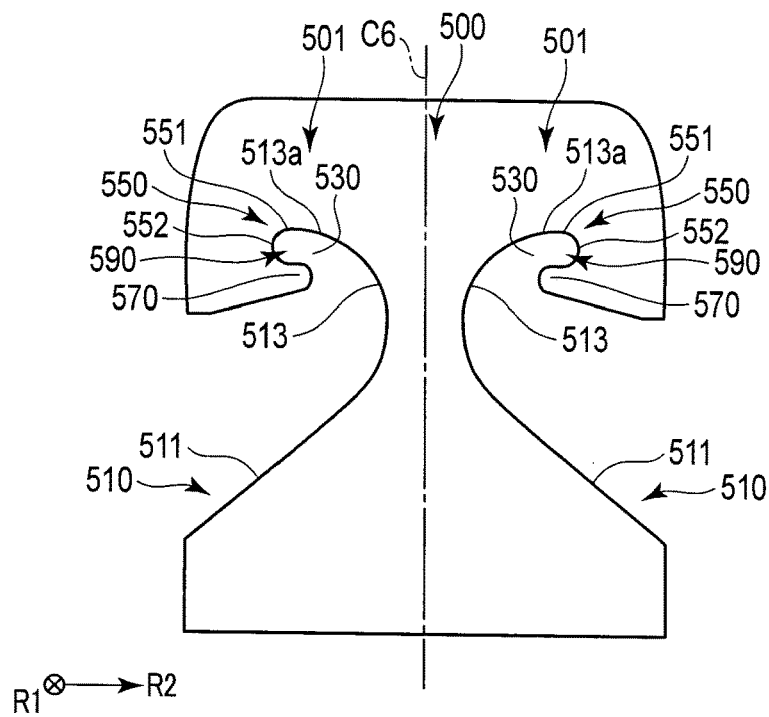
FIG. 2B is a front view of the holding mechanism.

As shown in FIGS. 1B, 2A and 2B, the holding mechanism 500 includes at least one holding unit 501, and each holding unit 501 includes a first guide portion 510, a second guide portion 513, an opening portion 530, a regulating/fixing portion 550 and a disengagement preventing portion 570. The first guide portion 510, second guide portion 513, opening portion 530, regulating/fixing portion 550 and disengagement preventing portion 570 are formed by working the thick plate portion of the holding mechanism 500. A description will be given of the case where two holding units 501 are provided.

In the present embodiment, the holding units 501 are arranged symmetric with respect to the central axis C6 of the holding mechanism 500, as shown in FIGS. 1B, 2A and 2B. One of the holding units 501 is arranged on the left side of the holding mechanism 500 with respect to a second radial direction R2 of the insertion opening portion 36a (i.e., a widthwise direction of the holding mechanism 500). The other holding unit 501 is arranged on the right side of the holding mechanism 500 with respect to the second radial direction R2 of the insertion opening portion 36a. When the holding mechanism 500 is viewed from the forceps plug portion 36 toward the grasp portion 33, one of the holding units 501 is arranged on the left side of the central axis C4 of the forceps plug portion 36, and the other holding unit 501 is arranged on the right side of the central axis C4 of the forceps plug portion 36.

As shown in FIGS. 1B, 2A and 2B, in the two holding units 501, the first guide portions 510 are on the same straight line in the second radial direction R2 of the insertion opening portion 36a and are adjacent to each other. The first guide portions 510 are not continuous with each other, and a thick plate portion of the holding mechanism 500 is located between the first guide portions 510. What was stated above holds true of the second guide portions 513, the opening portions 530, the regulating/fixing portions 550 and the disengagement preventing portions 570.

As shown in FIGS. 1B, 1C and 2A, the holding units 501 are not arranged parallel to each other, as viewed in the direction which is a lengthwise direction of the holding mechanism 500 from the forceps plug portion 36 to the grasp portion 33 and which is a first radial direction R1 of the insertion opening portion 36a perpendicular to the second radial direction R2. The holding units 501 are arranged on a straight line connecting the insertion opening portion 36a and a side portion of the grasp portion 33 of the operation portion 30, so that the proximal end portion 301 of the guide member 300, including the extension part 309 of part 303, can linearly extend to a side region of the grasp portion 33 from the insertion opening portion 36a, without striking against the grasp portion 33 of the operation portion 30. In other words, the holding units 501 are arranged such that the exposed proximal end portion of the guide member 300 can linearly extend from the forceps plug portion 36 toward the operator.

As shown in FIG. 1C, the holding units 501 are linearly arranged in such a manner as to form, for example, the shape of "V." The holding units 501 are arranged such that the insertion opening portion 36a of the forceps plug portion 36 is located at a bottom of the "V" shape and the grasp portion 33 is located between the lines of the "V" shape.

As shown in FIGS. 1B, 2A and 2B, one end portion of the first guide portion 510 is exposed to the outside, and the other end portion of the first guide portion 510 is continuous with one end portion of the regulating/fixing portion 550. The other end of the regulating/fixing portion 550 is continuous with one end portion of the disengagement preventing portion 570. The first guide portion 510, the regulating/fixing portion 550 and the disengagement preventing portion 570 are continuous circumferential faces of the holding mechanism 500, and the guide member 300 slide along these circumferential faces. In other words, the guide member 300 is movable along the circumferential faces. In this state, the guide member 300 is held in the order of the first guide portion 510, the second guide portion 513, the opening portion 530, the regulating/fixing portion 550 and the disengagement preventing portion 570. Each of these structural elements will be described.

As shown in FIGS. 1B and 3A, the first guide portion 510 is arranged such that part 305 is in the bent state and pressure contact state, and other exposed parts 303 (i.e., the held part 307 and part of extension part 309) are in contact with the first guide portion 510. In other words, the first guide portion 510 is arranged such that the held part 307 and part of the extension part 309 are in contact with the first guide portion 510 in the state where the bent/pressed part 305 is formed. The first guide portion 510 contacts part 303 of the guide member 300 and guides the guide member 300 in the state where the guide member 300 exposed to an outside of the insertion device from the insertion opening portion 36a of the insertion device 10 through that the guide member 300 is inserted, is bent. As shown in FIGS. 3A and 3B, the first guide portion 510 guides the held part 307 and part of the extension part 309 that contact the first guide portion 510, toward the second guide portion 513. The second guide portion 513 allows passage of part 303 (i.e., the held part 307 and part of the extension part 309), which has been guided by the first guide portion 510. The first guide portion 510 and the second guide portion 513 mentioned above serve as a smooth slide face on which the proximal end portion 301 of the guide member 300, including the held part 307 and part of the extension part 309, slides. The first guide portion 510 is shaped substantially in the shape of "J." The first guide portion 510 is located, for example, between the forceps plug portion 36 and the grasp portion 33, when viewed in the first radial direction R1.

As shown in FIG. 1B, the bent state mentioned above is intended to mean, for example, that the bent/pressed part 305 of part 303 is bent from the central axis (C5) direction of the insertion opening portion 36a (forceps plug portion 36) to a direction substantially perpendicular to the central axis (C5) direction, for example, in the shape of "L", and that the bent/pressed part 305 of part 303 is bent from the insertion opening portion 36a (forceps plug portion 36), for example, toward a side region of the grasp portion 33 of the operation portion 30. The side region is not a side region of the forceps plug portion 36; it is a side region of the grasp portion 33, as viewed in the second radial direction R2 which is a direction substantially perpendicular to the first radial direction R1 (which is a straight line connecting the forceps plug portion 36, the holding mechanism 500 and the gasp portion 33) and central axis (C3) direction of the grasp portion 33).

As shown in FIG. 1B, the pressure contact state is intended to mean that bending part 303 (bent/pressed part 305) is pressed against an inner circumferential face of the insert opening portion 36a (forceps plug portion 36) and an inner circumferential edge at an upper end of the insert opening portion 36a (forceps plug portion 36) from the insertion opening portion 36a (forceps plug portion 36) for example to the grasp portion 33 of the operation portion 30, and that bending part 303 is pressed against an upper end face of the forceps plug portion 36, which is a flat face on which the insertion opening portion 36a is arranged, from above the insertion opening portion 36a (forceps plug portion 36) and is thus positioned and fixed.

As shown in FIGS. 1B, 2A, 3A and 3B, the first guide portion 510 includes a contact portion 511 which comes into contact with the held part 307 and part of the extension part 309 of the part 303. The second guide portion 513 is located between the contact portion 511 and the regulating/fixing portion 550 in an introduction direction and is continuous with the contact portion 511 and the regulating/fixing portion 550. The second guide portion 513 permits the held part 307 and part of the extension par 309 of part 303 to be introduced from the contact portion 511 toward the regulating/fixing portion 550. In this manner, the first guide portion 510 introduces the held part 307 and part of the extension part 309 from the contact portion 511 toward the regulating/fixing portion 550 by means of the second guide portion 513.

Figure 2C:
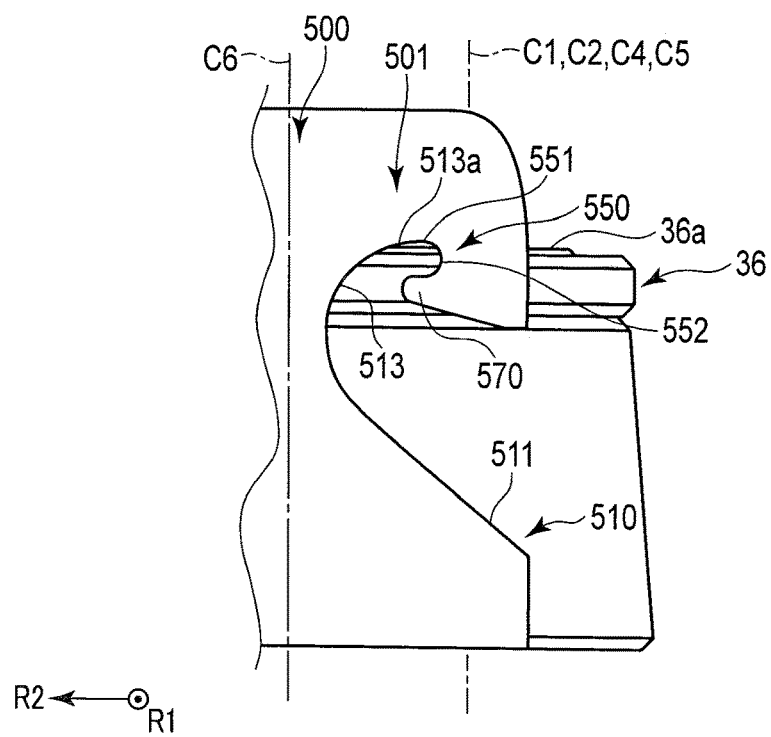
FIG. 2C illustrates how the height of each portion of the holding mechanism is related to an insertion opening portion.

As shown in FIGS. 1B, 2B and 2C, according to the present embodiment, the first guide portion 510 is slanted with reference to the flat face on which the insertion opening portion 36a is arranged so that the second guide portion 513 is arranged closer to the central axis C6 of the holding mechanism 500, which is parallel to the central axis C5 of the insertion opening portion 36a, than the contact portion 511, an end portion of the second guide portion 513 which is arranged on the side of the regulating/fixing portion 550 is arranged at the substantially same level as or at a lower level than the insertion opening portion 36a in the central axis (C5) direction of the insertion opening portion 36a, and the contact portion 511 is located farther from the central axis C6 of the holding mechanism 500 than the second guide portion 513 and is located at a position lower in level than the insertion opening portion 36a in the central axis (C5) direction of the insertion opening portion 36a. The contact portion 511 is arranged at a position lower in level than the second guide portion 513 in the central axis (C6) direction of the holding mechanism 500. The second guide portion 513 is arranged at a position toward which the bent/pressed part 305 returns to the original straight state from a bent state.

As shown in FIG. 2A, the contact portion 511 is a flat face and is wider than the second guide portion 513. As shown in FIG. 1B, a lowest portion of the contact portion 511 is higher in level than the flat face on which the forceps plug portion 36 is arranged and a lower end portion of the forceps plug portion 36. The contact portion 511 is slanted with reference to the forceps plug portion 36 and is also slanted with reference to the face on which the forceps plug portion 36 is arranged. To be more specific, the contact portion 511 is closer to the central axis C6 of the holding mechanism 500 at portions closer to the second guide portion 513 than at portions farther from the second guide portion 513.

As shown in FIGS. 3A and 3B, the guide member 300 is introduced from one end of the contact portion 511 to the other end thereof, which is continuous with the second guide portion 513. In order that the contact portion 511 can be exposed to the outside in the second radial direction R2 of the insertion opening portion 36a, the one end of the contact portion 511 outwardly expands more than a second regulating/fixing portion 552 (mentioned later) of the regulating/fixing portion 550 and disengagement preventing portion 570. In the second radial direction R2 of the insertion opening portion 36a, the other end of the contact portion 511 and the second guide portion 513 are arranged closer to the central axis 6 of the holding mechanism 500 than the regulating/fixing portion 550 and the disengagement preventing portion 570 and are covered with the regulating/fixing portion 550 and the disengagement preventing portion 570.

As shown in FIG. 2B, the second guide portion 513 is formed, for example, as one fourth of a complete circle. The second guide portion 513 is curved relative to the slanted contact portion 511 as if the second guide portion 513 falls toward the outer side of the holding mechanism 500. Part of the second guide portion 513 is opposed to the opening portion 530 and is covered with both the regulating/fixing portion 550 and the disengagement preventing portion 570.

As shown in FIG. 1C, the second guide portion 513 is linearly arranged such that the extension part 309 can linearly extend to a side region of the grasp portion 33 from the forceps plug portion 36 without striking against the grasp portion 33. The slope of the second guide portion 513 (the direction in which the second guide portion 513 is directed) with reference to the line connecting the central axis C5 of the insertion opening portion 36a and the central axis C3 of the grasp portion 33 is adjusted properly such that the extension part 309 can linearly extend to a side region of the grasp portion 33 from the forceps plug portion 36 without striking against the grasp portion 33. This feature may be applicable to the contact portion 511 as well.

As shown in FIGS. 2B and 2C, the second guide portion 513 has an end portion 513a adjacent to the first regulating/fixing portion 551 of the regulating/fixing portion 550. The end portion 513a is arranged substantially parallel to the flat face on which the insertion opening portion 36a is arranged (the second radial direction R2 of the insertion opening portion 36a). The end portion 513a has a desirable length in the second radial direction R2 of the insertion opening portion 36a such that the extension part 309 can linearly extend to a side region of the grasp portion 33 from the forceps plug portion 36 without striking against the grasp portion 33. In other words, as shown in FIG. 1B, the length of the end portion 513a in the second radial direction R2 of the insertion opening portion 36a is optimally adjusted such that the extension part 309 can linearly extend to a side region of the grasp portion 33 from the forceps plug portion 36 without striking against the grasp portion 33. Likewise, as shown in FIG. 1B, the slope of the end portion 513a (the direction in which end portion 513a is directed) with reference to the line connecting the central axis C5 of the insertion opening portion 36a and the central axis C3 of the grasp portion 33 is adjusted properly such that the extension part 309 can linearly extend to a side region of the grasp portion 33 from the forceps plug portion 36 without striking against the grasp portion 33. The end portion 513a is arranged at a position equal to or lower in level than the insertion opening portion 36a in the central axis (C5) direction of the insertion opening portion 36a.

As can be seen from the above, how the extension part 309 is arranged to a side region of the grasp portion 33 is determined, depending upon the direction of the second guide portion 513, the length of the end portion 513a and the direction of the end portion 513a.

As shown in FIG. 1B, the first guide portion 510 has a substantially triangular shape. The first guide portion 510 is tapered from the forceps plug portion 36 to the grasp portion 33, a distal end of a triangle is closer to the grasp portion 33 than to the forceps plug portion 36, and a bottom side of the triangle is closer to the forceps plug portion 36 than to the grasp portion 33. In oblique sides of the first guide portion 510, one oblique side includes a one end portion of the contact portion 511, is arranged away from the central axis C6 of the holding mechanism 500, and is included in the contact portion 511. The other of the oblique sides includes the other end of the contact portion 511 and is arranged close to the central axis C6 of the holding mechanism 500. The other of the oblique sides functions as the second guide portion 513 as well.

As shown in FIGS. 1B, 1C, 2A, 2B, 3A and 3B, the second guide portion 513, the regulating/fixing portion 550 and the disengagement preventing portion 570 define a structure which first extends away from the contact portion 511 of the first guide portion 510 and is then directed toward the contact portion 511 such that the proximal end portion 301 of the guide member 300, including the extension part 309 of part 303, can linearly extend to a side region of the grasp portion 33 of the operation portion 30 from the insertion opening portion 36a, without striking against the grasp portion 33 of the operation portion 30. In other word, the second guide portion 513, the regulating/fixing portion 550 and the disengagement preventing portion 570 define a structure as one unit which bends backward to the contact portion 511 of the first guide portion 510 such that the proximal end portion 301 can linearly extend to a side region of the grasp portion 33 from the insertion opening portion 36a, without striking against the grasp portion 33 of the operation portion 30.

Figure 2D:
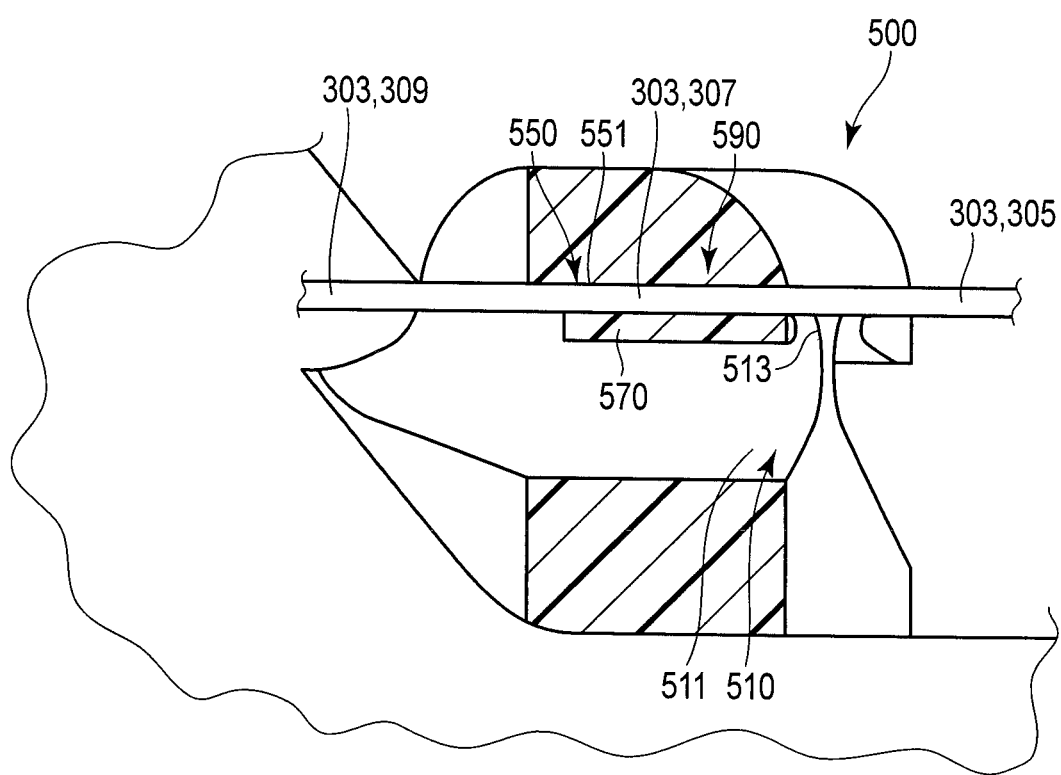
FIG. 2D is a longitudinal sectional view of the holding mechanism that holds the guide member.

As shown in FIGS. 2B and 3B, the opening portion 530, the regulating/fixing portion 550 and the disengagement preventing portion 570 jointly function as a concave elongated groove portion 590 with which the held part 307 is engageable. More specifically, as shown in FIGS. 3A and 3B, the regulating/fixing portion 550 and the disengagement preventing portion 570 jointly function as an engagement portion, where the held part 307 introduced by the first guide portion 510 is inserted through the opening portion 530 and engages with the regulating/fixing portion 550 and the disengagement preventing portion 570. As shown in FIG. 1B, the regulating/fixing portion 550 and the disengagement preventing portion 570 prevent the held part 307 from moving in the first radial direction R1 and the second radial direction R2. As shown in FIGS. 3A and 3B, the opening portion 530 is a portion where the held part 307 guided and introduced by the first guide portion 510 and the second guide portion 513 is inserted or pulled out. That is, the opening portion 530 enables the held part 307 from being inserted into or pulled out from the elongated groove portion 590. As shown in FIGS. 2A and 2B, the opening portion 530 and the regulating/fixing portion 550 jointly function, for example, as an L-shaped elongated groove. The elongated groove portion 590 communicates with the outside by way of the opening portion 530. As shown in FIGS. 1C and 2D, the elongated groove portion 590 communicates with an external region at both ends, as viewed in the central axis direction. One end of the elongated groove portion 590 is located on the side of the forceps plug portion 36, and the other end thereof is located on the grasp portion 33. The elongated groove portion 590 is not slanted with reference to the flat face on which the insertion opening portion 36a is arranged; it is substantially parallel to the flat face.

As shown in FIGS. 2A and 2B, an inner circumferential face of the L-shaped regulating/fixing portion 550 comes in contact with part of an outer circumferential face of the held part 307. With this structure, the L-shaped regulating/fixing portion 550 is designed such that the radius of curvature of a portion between one side of the L-shaped regulating/fixing portion 550 and the other side of the L-shaped regulating/fixing portion 550 is substantially the same as the radius of curvature of an outer shape of the held part 307. For example, the regulating/fixing portion 550 has a curve that is like one fourth of a complete circle.

As shown in FIGS. 2A and 2B, the opening portion 530, the regulating/fixing portion 550 and the disengagement preventing portion 570, which jointly define a concave shape, are arranged in such a manner as to cover an end portion of the second guide portion 513. The opening portion 530, regulating/fixing portion 550 and the disengagement preventing portion 570 are arranged above the first guide portion 510 in the central axis (C6) direction of the holding mechanism 500. As shown in FIG. 1B, the regulating/fixing portion 550 and the disengagement preventing portion 570 hold the held part 307 such that the held part 307 is perpendicular to both the central axis (C5) direction of the insertion opening portion 36a and the second radial direction R2, thereby enabling the bent state and the pressure contact state. The regulating/fixing portion 550 and the disengagement preventing portion 570 are substantially parallel to the flat face on which the insertion opening portion 36a is arranged. As shown in FIG. 1C, the regulating/fixing portion 550 and the disengagement preventing portion 570 are linearly arranged to a side region of the grasp portion 33 such that the proximal end portion 301 of the guide member 300 can linearly extend to a side region of the grasp portion 33 from the forceps plug portion 36 without striking against the grasp portion 33.

As shown in FIGS. 1B and 2A, the regulating/fixing portion 550 is continuous with the second guide portion 513. The regulating/fixing portion 550 is a portion into which the held part 307 inserted through the opening portion 530 is inserted. The regulating/fixing portion 550 is substantially parallel to the flat face on which the insertion opening portion 36a is arranged, such that a bent state and a pressure contact state can be maintained. The regulating/fixing portion 550 positions and fixes the held part 307 of part 303 so that the guide member 300, which has part 303 having passed the second guide portion 513 (i.e., the held part 307 and part of extension part 309) can maintain its bent state relative to the insertion opening portion 36a. In other words, the regulating/fixing part 550 regulates the movement of the held part 307 introduced by the second guide portion 513 and fixes the held part 307 in the movement regulated state, thereby maintaining the bent state and the pressure contact state. As shown in FIG. 2C, the regulating/fixing portion 550 is arranged at a position equal to or lower in level than the insertion opening portion 36a in the central axis (C5) direction of the insertion opening portion 36a.

As shown in FIGS. 1B and 4A, the regulating/fixing portion 550 fixes and positions part 303 of the guide member 300, with a tension applied to the guide member 300, so that the positioning and fixing state can be maintained even if the treatment tool 400 moves. To be more specific, the regulating/fixing portion 550 fixes and positions the held part 307, with the tension applied to both the bent/pressed part 305 and held part 307, so that the bent/pressed part 305 is prevented from moving when the treatment tool 400 is pulled off and the bent state and the pressure contact state can be maintained after the treatment tool 400 is pulled off. The regulating/fixing portion 550 positions and fixes the held part 307 such that the bent/pressed part 305 is prevented from being deformed and the bent/pressed is prevented from forming a loop portion 600 when the treatment tool 400 is pulled off.

The regulating/fixing portion 550 may be worked so that it causes an increased frictional resistance relative to the held part 307.

As shown in FIG. 2B, the regulating/fixing portion 550, which is shaped, for example, like "L", includes a first regulating/fixing portion 551 continuous with the end portion 513a of the second guide portion 513, and a second regulating/fixing portion 552 continuous with the first regulating/fixing portion 551. The first regulating/fixing portion 551 and the second regulating/fixing portion 552 are flat faces and function as wall portions. The second regulating/fixing portion 552 is continuous with the disengagement preventing portion 570.

As shown in FIGS. 2B and 2C, like the end portion 513a, the first regulating/fixing portion 551 is arranged substantially parallel to the flat face on which the insertion opening portion 36a is arranged (the second radial direction R2 of the insertion opening portion 36a). The first regulating/fixing portion 551 prevents the held part 307 (which is a portion of the part 303 inserted into the regulating/fixing portion 550) from moving upward from the regulating/fixing portion 550 in the central axis (C6) direction of the holding mechanism 500. In other words, the first regulating/fixing portion 551 serves as a stopper which prevents the held part 307 inserted into the regulating/fixing portion 550 from disengaging from the regulating/fixing portion 550 in the central axis (C6) direction of the holding mechanism 500. The first regulating/fixing portion 551 prevents the bent/pressed part 305 from being returned to the original linear state by the resilience of the guide member 300. The first regulating/fixing portion 551 is arranged at a position equal to or lower in level than the insertion opening portion 36a in the central axis (C5) direction of the insertion opening portion 36a.

As shown in FIG. 1C, the first regulating/fixing portion 551 has a desirable length in the second radial direction R2 of the insertion opening portion 36a such that the extension part 309 can linearly extend to a side region of the grasp portion 33 from the forceps plug portion 36 without striking against the grasp portion 33. In other words, the length of the first regulating/fixing portion 551, as measured in the second radial direction R2 of the insertion opening portion 36a, is optimally adjusted such that the extension part 309 can linearly extend to a side region of the grasp portion 33 from the forceps plug portion 36 without striking against the grasp portion 33.

As shown in FIGS. 2B and 2C, the second regulating/fixing portion 552 is arranged in the central axis (C6) direction of the holding mechanism 500, which is a direction perpendicular to the flat face on which the insertion opening portion 36a is arranged. The second regulating/fixing portion 552 prevents the held part 307 (which is a portion of the part 303 inserted into the regulating/fixing portion 550) from moving to the outside of the holding mechanism 500 from the regulating/fixing portion 550 in the second radial direction R2 of the insertion opening portion 36a. In other words, the second regulating/fixing portion 552 serves as a stopper which prevents the held part 307 inserted into the regulating/fixing portion 550 from disengaging from the regulating/fixing portion 550 in the second radial direction of the insertion opening portion 36a. The second regulating/fixing portion 552 mentioned above prevents the guide member 300 from rotating around the axis of the insertion opening portion 36a. In other words, the second regulating/fixing portion 552 positions and fixes the extension part 309 on the side of the grasp portion 33.

As shown in FIG. 1C, the second regulating/fixing portion 552 is linearly arranged such that the extension part 309 can linearly extend to a side region of the grasp portion 33 from the forceps plug portion 36 without striking against the grasp portion 33. In other words, the slope of the second regulating/fixing portion 552 (the direction in which the second regulating/fixing portion 552 is directed) with reference to the line connecting the central axis C5 of the insertion opening portion 36a and the central axis C3 of the grasp portion 33 is adjusted properly such that the extension part 309 can linearly extend to a side region of the grasp portion 33 from the forceps plug portion 36 without striking against the grasp portion 33.

As shown in FIGS. 3A and 3B, the second regulating/fixing portion 552 serves as a termination end portion where the sliding movement at the time of introduction ends. When the held part 307 comes into contact with the second regulating/fixing portion 552, the operation of positing and fixing the held part 307 ends, with the bent state and the pressure contact state maintained.

As shown in FIGS. 1B, 2A, 2B, 2C, 2D, 3A and 3B, the disengagement preventing portion 570 is continuous with the second regulating/fixing portion 552 of the regulating/fixing portion 550 and is substantially parallel to the flat face on which the insertion opening portion 36a is arranged. The disengagement preventing portion 570 prevents the held part 307 of part 303 from disengaging from the regulating/fixing portion 550 in the central axis (C6) direction of the holding mechanism 500. The disengagement preventing portion 570 functions as a placement face on which the part 303 positioned and fixed by the regulating/fixing portion 550 is placed, and also functions as a support face which supports the held part 307 of part 303. The disengagement preventing portion 570 is a flat surface portion. The disengagement preventing portion 570 prevents the held part 307 (which is inserted into the regulating/fixing portion 550) from moving downward of the holding mechanism 500 from the regulating/fixing portion 550 in the central axis (C6) direction of the holding mechanism 500. In other words, the disengagement preventing portion 570 serves as a stopper which prevents the held part 307 inserted into the regulating/fixing portion 550 from disengaging from the regulating/fixing portion 550 in the central axis (C6) direction of the holding mechanism 500. The disengagement preventing portion 570 prevents the guide member 300 from disengaging from the regulating/fixing portion 550 in the central axis (C6) direction of the holding mechanism 500, because of its own weight or an external force. The regulating/fixing portion 550 is linearly arranged such that the extension part 309 can linearly extend to a side region of the grasp portion 33 from the forceps plug portion 36 without striking against the grasp portion 33.

As shown in FIGS. 2B, 2D and 3B, the disengagement preventing portion 570 is opposed to the first regulating/fixing portion 551 of the regulating/fixing portion 550, which functions as an upper internal face of the holding mechanism 500. The disengagement preventing portion 570 is located away from the first regulating/fixing portion 551 of the regulating/fixing portion 550 by a distance corresponding to the diameter of the held part 307 of part 303. As shown in FIG. 2C, the placement face of the disengagement preventing portion 570 is arranged at a position equal to or lower in level than the insertion opening portion 36a in the central axis (C5) direction of the insertion opening portion 36a.

As shown in FIG. 2D, the regulating/fixing portion 550 and the disengagement preventing portion 570 have predetermined lengths along which they are in plane contact with the held part 307. It is to be noted here that the regulating/fixing portion 550 and the disengagement preventing portion 570 are not in point contact with the guide member 300.

The holding mechanism 500 mentioned above holds the guide member 300 which reaches the subject to guide the treatment tool 400 thereto, and when the subject is treated with the treatment tool 400 inserted into the treatment tool insertion channel from the insertion opening portion 36a and projected from the distal end opening portion. To be more specific, the holding mechanism 500 holds the held part 307 which comes out of the forceps plug portion 36 and exposed to the outside of the insertion device 10, such that the guide member 300 is fixed and is prevented from being shifted in position.

As shown in FIG. 1B, the holding mechanism 500 holds part 307 such that the bent state and pressure contact state of part 305 are maintained and the extension part 309 is positioned and fixed to a side position.

As shown in FIG. 1B, the guide member 300 is positioned and fixed at two portions, namely, the bent/pressed part 305 which is bent relative to the insertion opening portion 36a and pressed against the insertion opening portion 36a, and the held part 307 which is positioned, fixed and held by the regulating/fixing portion 550. Fixed at these two portions, the guide member 300 is prevented from being shifted in position.

[Operation]

By way of example, a description will be given as to how the guide member 300 guides the treatment tool 400 to the duodenal papilla.

[Operation of Guiding Treatment Tool 400]

The guide member 300 is engaged with a groove portion (not shown) of the treatment tool 400. The groove portion extends in the axial direction of the treatment tool 400, for example, along the whole length of the treatment tool 400. The proximal end portion 301 of the guide member 300 is outside the groove portion and separate from the treatment tool 400. That is, the guide member 300 and the distal end portion of the treatment tool 400 are integral with each other, but the proximal end portion is separate from them, as can be seen in FIGS. 1B and 4A.

In this state, the guide member 300 and the treatment tool 400 are inserted from the insertion opening portion 36a into the interior of the insertion device 10 by way of the forceps plug portion 36 and the treatment tool insertion opening portion 35a. The guide member 300 and the treatment tool 400 are inserted through the treatment tool insertion channel and are projected from the distal opening portion to the side position of the distal end portion of the insertion portion 20. The distal end portion of the guide member 300 reaches the subject such as the bile duct and becomes ready to guide the treatment tool 400 to the subject. The proximal end portion 301 of the guide member 300 and the proximal end portion of the treatment tool 400 are projected out of the insertion opening portion 36a and are thus exposed outside the insertion device 10.

In the above state, the guide member 300 and the treatment tool 400 are operated by the operation of the right hand of the operator, with the grasp portion 33 being grasped by the left hand of the operator.

[Bending and Pressing in Holding Operation]

Of the exposed proximal end portion 301 of the guide member 300 which is outside the groove portion and the insertion device 10, the part 303 is held by one of the holding units 501.

To be specific, the part 303 is bent in the shape of "L" relative to the insertion opening portion 36a and is pulled from the forceps plug portion 36 side toward the grasp portion 33 side. As a result, the part 303 is pressed against the inner circumferential face of the insertion opening portion 36a (forceps plug portion 36) and the inner circumferential edge of the upper end side, and is also pressed against the upper end face of the forceps plug portion 36 from above the insertion opening portion 36a (forceps plug portion 36). As a result, the bent/pressed part 305 is formed, and the bent state and the pressure contact state are maintained.

Provided that the bent/pressed part 305 is formed, and the bent state and the pressure contact state are maintained, the guide member 300 does not have to be pulled.

The bending and pressing operation described above may be omitted, and the bent/pressed part 305 may be formed during a guide operation or a positioning/fixing operation, mentioned below.

[Introduction in Holding Operation]

As shown in FIGS. 3A and 3B, the first guide portion 510 guides the held part 307 and part of the extension part 309, which come in contact with the first guide portion 510, toward the regulating/fixing portion 550 by way of the second guide portion 513 in a state where the bent/pressed part 305 is formed.

To be specific, as shown in FIGS. 3A and 3B, the held part 307 and part of the extension part 309 come in contact with the contact portion 511. The held part 307 and part of extension part 309 slide on the contact the contact portion 511 and move closer to the second guide portion 513. The held part 307 slides on the second guide portion 513, passes through the opening portion 530, and moves closer to the regulating/fixing portion 550. In this manner, the held part 307 moves along the first guide portion 510 and the second guide portion 513 toward the regulating/fixing portion 550. In other words, the held part 307 slides on the first guide portion 510 and the second guide portion 513 along the first guide portion 510 and the second guide portion 513.

The part 303 merely comes into contact with the first guide portion 510 and slides on the first guide portion and the second guide portion 513. Therefore, the operator can perform this introduction operation in a blind state.

The contact portion 511 and the second guide portion 513 are arranged at a position equal to or lower in level than the insertion opening portion 36a. Therefore, even if part 303 has been introduced, the bent state and the pressure contact state are maintained at the bent/pressed part 305.

The second guide portion 513 is arranged near the central axis C6 of the holding mechanism 500 and at a position equal to or lower in level than the insertion opening portion 36a. The contact portion 511 is arranged away from the central axis C6 of the holding mechanism 500 and at a position lower in level than the insertion opening portion 36a. The first guide portion 510 is slanted with reference to the flat face on which the insertion opening portion 36a is arranged. Therefore, the held part 307 and part of the extension part 309 easily move on the first guide portion 510 and the second guide portion 513.

The contact portion 511 is arranged at a position lower in level than the second guide portion 513, and the second guide portion 513 is covered with the regulating/fixing portion 550. As a result, the held part 307 and part of the extension part 309 first come into reliable contact with the contact portion 511.

The contact portion 511 and the second guide portion 513 function as smooth sliding faces. Therefore, the held part 307 can be easily introduced by merely pushing it against the first guide portion 510 and the second guide portion 513.

The contact portion 511 extends outward more than the regulating/fixing portion 550 and the disengagement preventing portion 570. As a result, the held part 307 and part of the extension part 309 can easily come into contact with the contact portion 511.

The second guide portion 513 is arranged at a position which is higher in level than the contact portion 511 and toward which part 305 returns to the original straight state from a bent state. Therefore, the introduction operation does not impose a burden on the operator. The movement of the guide member 300 is assisted by the resilience.

Therefore, the operator can easily perform the introduction operation (which is for fixing the held part 307) in a blind state.

In the introduction operation, the guide member 300 is operated by the operation of the right hand of the operator, with the grasp portion 33 held by the left hand of the operator.

[Positioning/Fixing in Holding Operation]

As shown in FIGS. 3A and 3B, the held part 307 slides on the second guide portion 513, passes through the opening portion 530, is inserted into the regulating/fixing portion 550 (which is an elongated groove portion 590 having a concave shape) and the disengagement preventing portion 570, and engages with the regulating/fixing portion 550 and the disengagement preventing portion 570. In this manner, part 303 moves inside the elongated groove portion 590 along the regulating/fixing portion 550 and the disengagement preventing portion 570.

As a result, the regulating/fixing part 550 regulates the movement of the held part 307, with the bent state and the pressure contact state maintained, and positions and fixes the held part 307 in the movement regulated state. The disengagement preventing portion 570 prevents the held part 307 from disengaging from the regulating/fixing portion 550. The guide member 300 is positioned and fixed at two portions, namely, the bent/pressed part 305 and held part 307, and is thus prevented from being shifted in position.

After sliding on the first guide portion 510 and the second guide portion 513, the held part 307 is merely inserted into the regulating/fixing portion 550. Therefore, the operator can perform this positioning/fixing operation in a blind state.

The regulating/fixing portion 550 and the disengagement preventing portion 570 are substantially parallel to the flat face on which the insertion opening portion 36a is arranged. In other words, they are arranged substantially perpendicular to the central axis (C5) direction of the insertion opening portion 36a. Therefore, the regulating/fixing portion 550 and the disengagement preventing portion 570 hold the held part 307 such that the held part 307 is perpendicular to the central axis (C5) direction of the insertion opening portion 36a. As a result, the bent state and the pressure contact state are maintained.

The regulating/fixing portion 550 is arranged at a position equal to or lower in level than the insertion opening portion 36a in the central axis (C5) direction of the insertion opening portion 36a. As a result, the bent state and the pressure contact state are maintained.

The first regulating/fixing portion 551 prevents the held part 307 (which is a portion inserted into the regulating/fixing portion 550) from moving upward from the regulating/fixing portion 550 in the central axis (C6) direction of the holding mechanism 500. In other words, the first regulating/fixing portion 551 prevents the held part 307 inserted into the regulating/fixing portion 550 from disengaging from the regulating/fixing portion 550 in the central axis (C6) direction of the holding mechanism 500. The first regulating/fixing portion 551 prevents the bent/pressed part 305 from being returned to the original linear state by the resilience of the guide member 300.

The second regulating/fixing portion 552 prevents the held part 307 inserted into the regulating/fixing portion 550 from moving outward of the holding mechanism 500 from the regulating/fixing portion 550 in the second radial direction R2 of the insertion opening portion 36a. In other words, the second regulating/fixing portion 552 prevents the held part 307 inserted into the regulating/fixing portion 550 from disengaging from the regulating/fixing portion 550 in the second radial direction R2 of the insertion opening portion 36a. The second regulating/fixing portion 552 mentioned above prevents the guide member 300 from rotating around the axis of the insertion opening portion 36a. In other words, the second regulating/fixing portion 552 positions and fixes the extension part 309 on the side of the grasp portion 33.

The second regulating/fixing portion 552 serves as a termination end portion where the sliding movement at the time of introduction ends. When the held part 307 comes into contact with the second regulating/fixing portion 552, the operator is informed that the held part 307 is positioned and fixed in the state where the bent state and the pressure contact state are maintained.

Where the regulating/fixing portion 550 is so worked as to cause an increased frictional resistance, the held part 307 can be reliably positioned and fixed.

The disengagement preventing portion 570 is substantially parallel to the flat face on which the insertion opening portion 36a is arranged, and is located lower in level than the flat face. As a result, the bent state and the pressure contact state are maintained. The disengagement preventing portion 570 prevents the held part 307 (which is inserted into the regulating/fixing portion 550) from moving downward from the regulating/fixing portion 550 in the central axis (C6) direction of the holding mechanism 500. In other words, the disengagement preventing portion 570 prevents the held part 307 inserted into the regulating/fixing portion 550 from disengaging from the regulating/fixing portion 550 in the central axis (C6) direction of the holding mechanism 500.

The above operation can be performed reliably since the disengagement preventing portion 570 functions as both a placement face and a support face.

The disengagement preventing portion 570 is opposed to the first regulating/fixing portion 551 and is located away from the first regulating/fixing portion 551 by the distance corresponding to the diameter of the held part 307. With this structure, the held part 307 is prevented from shaking at the regulating/fixing portion 550 and the disengagement preventing portion 570. When the held part 307 is inserted into the elongated groove portion 590, the operator feels the held part 307 click and is thereby informed that the held part 307 has been inserted into the elongated groove portion 590 and has been positioned and fixed.

The disengagement preventing portion 570 is located lower in level than the flat face on which the insertion opening portion 36a is arranged. As a result, the bent state and the pressure contact state are maintained.

The first guide portion 510, second guide portion 513, opening portion 530, regulating/fixing portion 550 and disengagement preventing portion 570 are arranged on a straight line connecting the insertion opening portion 36a and a side position of the operation portion 30. With this structure, the extension part 309 can linearly extend to a side region of the grasp portion 33 from the forceps plug portion 36 without striking against the grasp portion 33.

The second guide portion 513, the regulating/fixing portion 550 and the disengagement preventing portion 570 define a structure which first extends away from the contact portion 511 and is then directed toward the contact portion 511. With this structure, the extension part 309 can linearly extend to a side region of the grasp portion 33 from the forceps plug portion 36 without striking against the grasp portion 33.

The regulating/fixing portion 550 and the disengagement preventing portion 570 have predetermined lengths along which they are in plane contact with part 303. With this structure, the held part 307 can be reliably positioned and fixed.

The lengths and directions of the second guide portion 513, regulating/fixing portion 550 and disengagement preventing portion 570 are adjusted in a desirable manner. With this structure, the extension part 309 can linearly extend to a side region of the grasp portion 33 from the forceps plug portion 36 without striking against the grasp portion 33.

Therefore, the operator can easily fix and position the held part 307 in a blind state.

In the positioning/fixing operation, the guide member 300 is operated by the right hand of the operator, with the grasp portion 33 held by the left hand of the operator.

[Replacement and Disengaging Operations of Treatment Tool 400]

When the treatment tool 400 is replaced with another treatment tool, only the treatment tool 400 is pulled such that it is peeled from the guide member 300, as shown in FIG. 4A. The treatment tool 400 is detached from the insertion device 10.

After the treatment tool 400 is detached from the insertion device 10, the held part 307 is temporarily removed from the holding mechanism 500 in the order opposite to that described above and shown in FIGS. 3A and 3B. The held part 307 merely moves along the disengagement preventing portion 570, regulating/fixing portion 550, second guide portion 513 and first guide portion 510.

That is, when the held part 307 is released from the positioned and fixed state, the held part 307 merely slides along the disengagement preventing portion 570, regulating/fixing portion 550, second guide portion 513 and first guide portion 510. Therefore, the operator can easily perform this disengagement operation in a blind state.

In this state, the distal end of the guide member 300 is projected from the distal opening portion.

Another treatment tool 400 having a monorail section is guided along the guide member 300 by means of the monorail section and is inserted from the insertion opening portion 36a into the insertion device 10. The treatment tool 400 is moved along the guide member 300, extends from the distal opening portion, and reaches the subject.

In this manner, the treatment tool 400 for replacement is guided to the subject by the guide member 300.

After the treatment tool 400 is guided, the proximal end portion 301 of the guide member 300 is exposed, and part 303 of the exposed portion is held by one of the holding units 501, as shown in FIGS. 3A and 3B.

In the replacement operation and the disengagement operation, the guide member 300 and the treatment tool 400 are operated by the right hand of the operator, with the grasp portion 33 held by the left hand of the operator.

[Prevention of Deformation of Bent/Pressed Part 305 when Replacement Operation is Performed]

When the treatment tool 400 is pulled for replacement, as shown in FIG. 4A, the tensile force generated then is applied to the bent\pressed part 305 of the guide member 300 in the central axis (C5) direction of the insertion opening portion 36a. The application of the tensile force releases the bent\pressed part 305 from the bent state and the pressure contact state, and a portion of the guide member 300 which has come out of the forceps plug portion 36 tends to form a loop portion 600. A deformation, including this loop portion 600, is caused when the treatment tool 400 inserted into the insertion device 10 is pulled by the tensile force. In this case, the proximal end portion side of the guide member 300, including the held part 307, is positioned and fixed in the holding mechanism 500 by the holding mechanism 500, while the distal end portion of the guide member 300 may be shifted in position as a result of the deformation. To be more specific, the distal end portion may be pulled into the insertion device 10 from the distal opening portion, and a positional shift like this may happen at the distal end portion.

However, the regulating/fixing portion 550 is substantially parallel to the flat face on which the insertion opening portion 36a is arranged, such that a bent state and a pressure contact state can be maintained. The regulating/fixing portion 550 is arranged at a position equal to or lower in level than the insertion opening portion 36 in the central axis (C5) direction of the insertion opening portion 36a. The regulating/fixing portion 550 fixes and positions the held part 307, with the tension applied to both the bent/pressed part 305 and the held part 307. The holding mechanism 500 is arranged adjacent to the insertion opening portion 36a. The holding mechanism 500 is arranged in the grasp portion 33. Even when the treatment tool 400 is pulled off, the bent/pressed part 305 is prevented from moving, and the bent state and the pressure contact state are maintained. The bent/pressed part 305 is prevented from being deformed and is prevented from forming the loop portion 600 when the treatment tool 400 is pulled off. That is, even if the tensile force is generated, the deformation is prevented, the formation of a loop portion 600 is prevented, and the bent state and the pressure contact state is maintained.

The formation of the loop portion 600 is also prevented by the guide member 300 being positioned and fixed at two portions, namely, the bent/pressed part 305 and held part 307.

As a result, the distal end portion of the guide member 300 is prevented from being shifted in position.

Figure 4B:
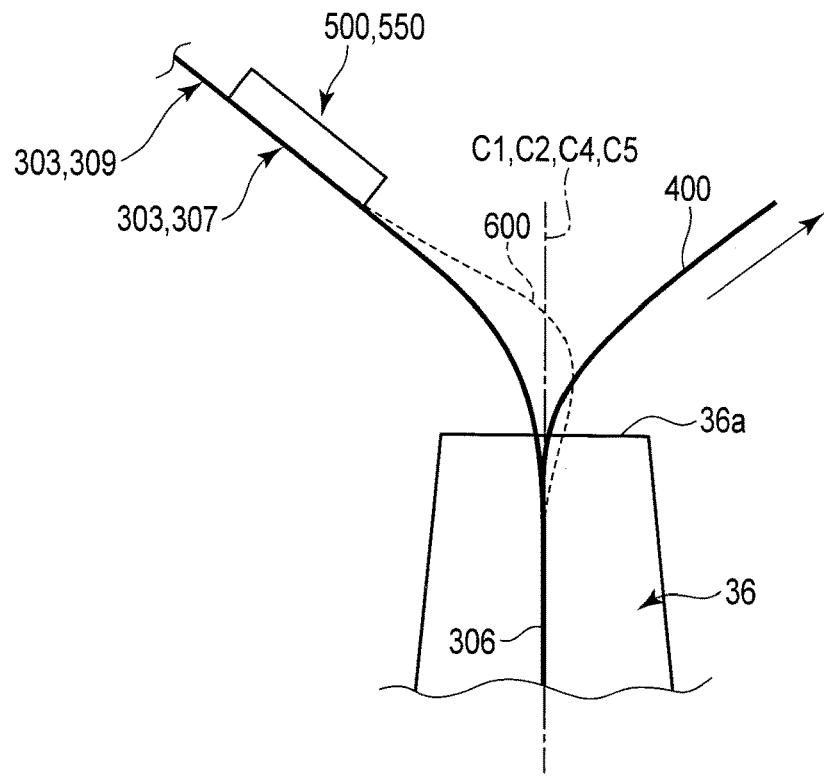
FIG. 4B illustrates an example illustrating how a fixing force decreases at the bent/pressed part.

Let us assume that unlike the present embodiment, the regulating/fixing portion 550 is arranged at a position higher in level than the insertion opening portion 36a in the central axis (C5) direction of the insertion opening portion 36a, as shown in FIG. 4B. In this case, the bent\pressed part 305 is released from the bent and pressure contact state, and the pressure contact state is not maintained. Only the held part 307 is positioned and fixed. As compared with the present embodiment, the fixing force decreases. Accordingly, when the treatment tool 400 is pulled off, a deformation is generated. A loop portion 600 is formed, and the distal end portion is inevitably shifted in position. Even if the loop portion 600 is not generated, a slight deformation may occur, leading to the positional shift at the distal end portion.

Figure 4C:
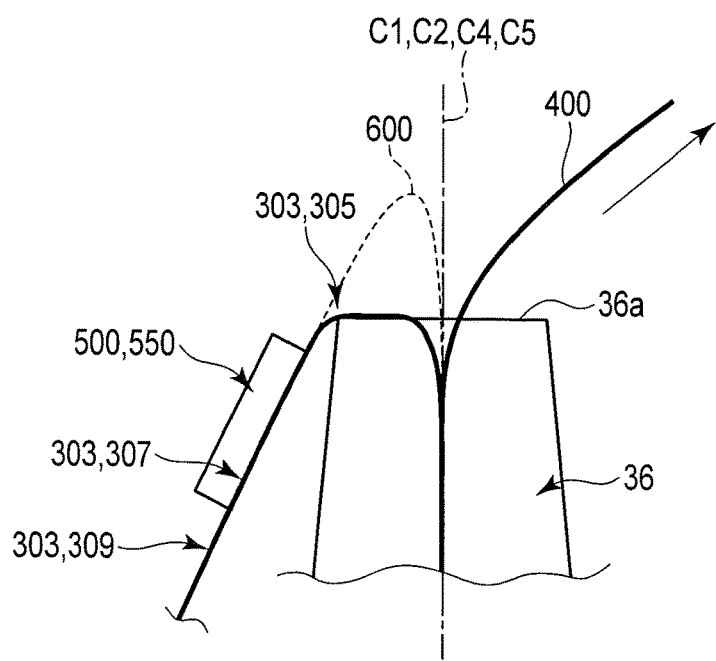
FIG. 4C illustrates an example illustrating how the fixing force decreases at the bent/pressed part.

Let us assume that, as in the present embodiment, the regulating/fixing portion 550 is arranged at a position lower in level than the insertion opening portion 36a in the central axis (C5) direction of the insertion opening portion 36a, as shown in FIG. 4C, but that the regulating/fixing portion 550 is not substantially parallel to the flat face (on which the insertion opening portion 36a is arranged), as in the present embodiment, but is slanted relative to the insertion opening portion 36a. In this case, since the tensile force acts in the central axis (C5) direction, a deformation is generated, a loop portion 600 is formed, and the distal end portion is inevitably shifted in position. Even if the loop portion 600 is not formed, the bent state and the pressure contact state fail to be maintained and the fixing at the bent/pressed part 305 may loosen, if a slight deformation is generated.

These points can be pointed out even if the regulating/fixing portion 550 is arranged at a position higher in level than the insertion opening portion 36a, or if the regulating/fixing portion 550 is arranged in the central axis (C5) direction of the insertion opening portion 36a.

In the present embodiment, however, the deformation is prevented, the formation of a loop portion 600 is prevented, and the bent state and the pressure contact state are maintained. In the present embodiment, the fixing at the bent/pressed part 305 is prevented from loosening, and the distal end portion is prevented from being shifted in position.

Thus, the guide member 300 reliably guides the treatment tool 400 for replacement.

The above-mentioned guide operation of the treatment tool 400, the holding operation thereof (including a bending and pressing operation, an introduction operation, and a positioning/fixing operation), the replacement operation of the treatment tool 400, and the releasing operation are performed using one of the holding units 501. These operations may be performed using the other holding unit 501. The operations are similar irrespective of which holding unit 501 is used.

In a surgical operation using two or more treatment tools 400, the operations mentioned above are performed using both holding units 501. If the elongated groove portion 590 is deep, a single holding unit 501 can be designed to hold a plurality of guide members 300 side by side. As described above, the present embodiment is advantageously applied to an operation that employs a two or more treatment tools.

[Advantages]

As described above, according to the present embodiment, the first guide portion 510 guides the held part 307 and part of the extension part 309 which come in contact with the first guide portion 510 toward the regulating/fixing portion 550 by way of the second guide portion 513 in a state where the bent/pressed part 305 is formed. The regulating/fixing portion 550 is continuous with the second guide portion 513. With this structure, the present embodiment is only required to move the held part 307 along the first guide portion 510, second guide portion 513, and regulating/fixing portion 550.

Therefore, the embodiment enables both the positioning/fixing operation and the disengaging operation to be performed in the blind state. In other words, the operator does not have to visually confirm the positioning/fixing operation or the disengaging operation, thereby the load on the operator is thus reduced, and the operator can concentrate his or her attention to another operation.

The regulating/fixing portion 550 is substantially parallel to the flat face on which the insertion opening portion 36a is arranged, such that a bent state and a pressure contact state can be maintained. The regulating/fixing part 550 regulates the movement of part 303 introduced by the first guide portion 510 and the second guide portion 513 and fixes the held part 303 in the movement regulated state, thereby maintaining the bent state, the pressure state and the positing and fixing.

Accordingly, the present embodiment prevents the guide member 300 from being shifted in position.

The regulating/fixing portion 550 and the disengagement preventing portion 570 are substantially parallel to the flat face on which the insertion opening portion 36a is arranged. Therefore, the regulating/fixing portion 550 and the disengagement preventing portion 570 hold the held part 307 such that the held part 307 is perpendicular to the central axis (C5) direction of the insertion opening portion 36a. Accordingly, the present embodiment can maintain both a bent state and a pressure contact state.

The regulating/fixing portion 550 is arranged at a position equal to or lower in level than the insertion opening portion 36a in the central axis (C5) direction of the insertion opening portion 36a. Accordingly, the present embodiment can maintain both a bent state and a pressure contact state.

The regulating/fixing portion 550 fixes and positions the held part 307, with the tension applied to both the bent/pressed part 305 and held part 307. With this structure, the present embodiment prevents the bent/pressed part 305 from moving when the treatment tool 400 is pulled off, and the bent state and the pressure contact state can be maintained even if the treatment tool 400 is pulled off or moved. The present embodiment prevents the bent/pressed part 305 from being deformed and also prevents formation of the loop portion 600 even if the treatment tool 400 is pulled off.

According to the present embodiment, the first regulating/fixing portion 551 prevents the held part 307 (which is a portion inserted into the regulating/fixing portion 550) from moving upward from the regulating/fixing portion 550 in the central axis (C6) direction of the holding mechanism 500. According to the present embodiment, the first regulating/fixing portion 551 prevents the bent/pressed part 305 from being returned to the original linear state by the resilience of the guide member 300.

According to the present embodiment, the second regulating/fixing portion 552 prevents the held part 307 inserted into the regulating/fixing portion 550 from moving outward of the holding mechanism 500 from the regulating/fixing portion 550 in the second radial direction R2 of the insertion opening portion 36a. According to the present embodiment, the second regulating/fixing portion 552 prevents the guide member 300 from rotating around the axis of the insertion opening portion 36a.

According to the present embodiment, when the held part 307 comes into contact with the second regulating/fixing portion 552, the operator is informed that the held part 307 is positioned and fixed in the state where the bent state and the pressure contact state are maintained.

According to the present embodiment, the second regulating/fixing portion 552 serves as a termination end portion where the sliding movement at the time of introduction ends. When the held part 307 comes into contact with the second regulating/fixing portion 552, the operator is informed that held part 307 is positioned and fixed in the state where the bent state and the pressure contact state are maintained.

According to the present embodiment, where the regulating/fixing portion 550 is so worked as to cause an increased frictional resistance, the held part 307 can be reliably positioned and fixed.

The first guide portion 510 is slanted with reference to the flat face on which the insertion opening portion 36a is arranged. With this structure, the present embodiment enables the held part 307 and part of extension part 309 to easily move along the first guide portion 510.

The contact portion 511 is arranged at a position lower in level than the second guide portion 513, and the second guide portion 513 is covered with the regulating/fixing portion 550. According to the present embodiment, therefore, the held part 307 and part of the extension part 309 first come into reliable contact with the contact portion 511.

The contact portion 511 and the second guide portion 513 function as smooth sliding faces. With this structure, the present embodiment is only required to move the held part 307 along the first guide portion 510 and second guide portion 513 when it is introduced.

The contact portion 511 extends outward more than the regulating/fixing portion 550 and the disengagement preventing portion 570. According to the present embodiment, therefore, the held part 307 and part of the extension part 309 can easily come into reliable contact with the contact portion 511.

The second guide portion 513 is arranged at a position which is higher in level than the contact portion 511 and toward which part 305 returns to the original straight state from a bent state. According to the present embodiment, therefore, the introduction operation can be performed without imposing a burden on the operator. According to the present embodiment, the movement of the guide member 300 is assisted by the resilience.

According to the present embodiment, the disengagement preventing portion 570 prevents the held part 307 from dropping off.

The disengagement preventing portion 570 is substantially parallel to the flat face on which the insertion opening portion 36a is arranged, and is located lower in level than the flat face. Accordingly, the present embodiment can maintain both a bent state and a pressure contact state. According to the present embodiment, the disengagement preventing portion 570 prevents the held part 307 (which is a portion inserted into the regulating/fixing portion 550) from moving downward from the regulating/fixing portion 550 in the central axis (C6) direction of the holding mechanism 500.

The disengagement preventing portion 570 functions as both the placement face and the support face. According to the present embodiment, therefore, the above operations can be performed reliably.

The disengagement preventing portion 570 is opposed to the first regulating/fixing portion 551 and is located away from the first regulating/fixing portion 551 by the distance corresponding to the diameter of the held part 307. With this structure, the present embodiment prevents the held part 307 from shaking at the regulating/fixing portion 550 and the disengagement preventing portion 570. When the held part 307 is inserted into the elongated groove portion 590, the operator feels the held part 307 click and is thereby informed that the held part 307 has been inserted into the elongated groove portion 590 and has been positioned and fixed.

At least one holding unit 501 is provided. Because of this, the present embodiment is advantageously applied to a surgical operation wherein a plurality of treatment tools 400 are used. One of the holding units 501 need not be same in size as the other holding unit 501. This size is intended to mean, for example, the size of the elongated groove portion. Therefore, the present embodiment is advantageously applied to a surgical operation wherein a plurality of treatment tools 400 having various thicknesses are used.

The first guide portion 510, second guide portion 513, opening portion 530, regulating/fixing portion 550 and disengagement preventing portion 570 are arranged on a straight line connecting the insertion opening portion 36a and a side region of the operation portion 30. With this structure of the present embodiment, the extension part 309 can linearly extend to a side region of the grasp portion 33 from the forceps plug portion 36 without striking against the grasp portion 33. According to the present embodiment, therefore, the operator can easily hold the extension part 309.

The second guide portion 513, the regulating/fixing portion 550 and the disengagement preventing portion 570 define a structure which first extends away from the contact portion 511 of the first guide portion 510 and is then directed toward the contact portion 511. With this structure of the present embodiment, the extension part 309 can linearly extend to a side region of the grasp portion 33 from the forceps plug portion 36 without striking against the grasp portion 33. According to the present embodiment, the operator can easily hold the extension part 309.

The regulating/fixing portion 550 and the disengagement preventing portion 570 have predetermined lengths along which they are in plane contact with part 303. With this structure of the present embodiment, the held part 307 can be reliably positioned and fixed.

If, unlike the present embodiment, the bent/pressed part 305 is located away from the held part 307, the portion between the bent/pressed part 305 and the held part 307 may flex and move even if the held part 307 is positioned and fixed. As a result, the bent state and the pressed state may not be maintained. If this happens, the portion in question may be deformed, with the result that a loop portion 600 may be formed and the distal end portion of the guide member 300 may be shifted in position.

In the present embodiment, however, the holding mechanism 500 is arranged adjacent to the insertion opening portion 36a, namely, to the operation portion 30. Since, in the present embodiment, the bent/pressed part 305 and the held part 307 can be continuous and adjacent to each other, the bent state and the pressed state are maintained, and the guide member 300 can be positioned and fixed at two portions, namely, the bent/pressed part 305 and the held part 307.

The holding mechanism 500 is a mechanism integrally formed with the operation portion 30 or a mechanism removable from the operation portion 30. Where the holding mechanism 500 is integral with the operation portion 30, it can be cleaned together with the operation portion 30. Where the holding mechanism 500 is a separate mechanism from the operation portion 30, it can be designed in such a manner that treatment tools 400 of various thicknesses can be employed.

The guide member 300 is positioned and fixed by the holding mechanism 500 at two portions, namely, the bent/pressed part 305 and held part 307. With this structure of the embodiment, the bent/pressed part 305 is prevented from being deformed, the formation of a loop portion 600 can be reliably prevented, and the guide member 300 is reliably prevented from being shifted in position.

The guide member 300 has resilience and is thus inhibited from having the bending tendency. Therefore, the present embodiment can be applied to the case where the guide member 300 is not held by the holding mechanism 500.

It is to be noted that the disengagement preventing member 570 is not necessarily required as long as the regulating/fixing part 550 can be positioned and fixed.

[Modification of Holding Mechanism 500]

In the above-mentioned embodiment, the holding mechanism 500 is provided in the operation portion 30. However, the present embodiment is not limited to this structure as long as the holding mechanism 500 is arranged adjacent to the insertion opening portion 36a. For example, the holding mechanism 500 may be provided in the forceps plug portion 36.

In this case, the holding mechanism 500 is integrally formed with the forceps plug portion 36, as shown in FIG. 5A, or is a removable separate mechanism though illustration of this structure is omitted.

Where the holding mechanism 500 is integrally formed with the forceps plug portion 36, the holding mechanism 500 is provided in the insertion device 10 such that the holding mechanism 500 is located at the position described in connection with the above embodiment. The holding mechanism 500 having this structure is formed by insert molding, together with the forceps plug portion 36.

Where the holding mechanism 500 is a separate mechanism made independently of the forceps plug portion 36, the holding member 500 is detachably attached to the forceps plug portion 36. In this case, the holding mechanism 500 comprises a belt member to be wound around the forceps plug portion 36, and the belt member enables the holding mechanism 500 to be removably attached to the forceps plug portion 36.

With this structure, the holding mechanism 500 can be removably attached to the insertion device 10, together with the forceps plug portion 36. The holding mechanism 500 and the forceps plug portion 36 may be disposable.

[Modification of Opening Portion 530]

Figure 5B:
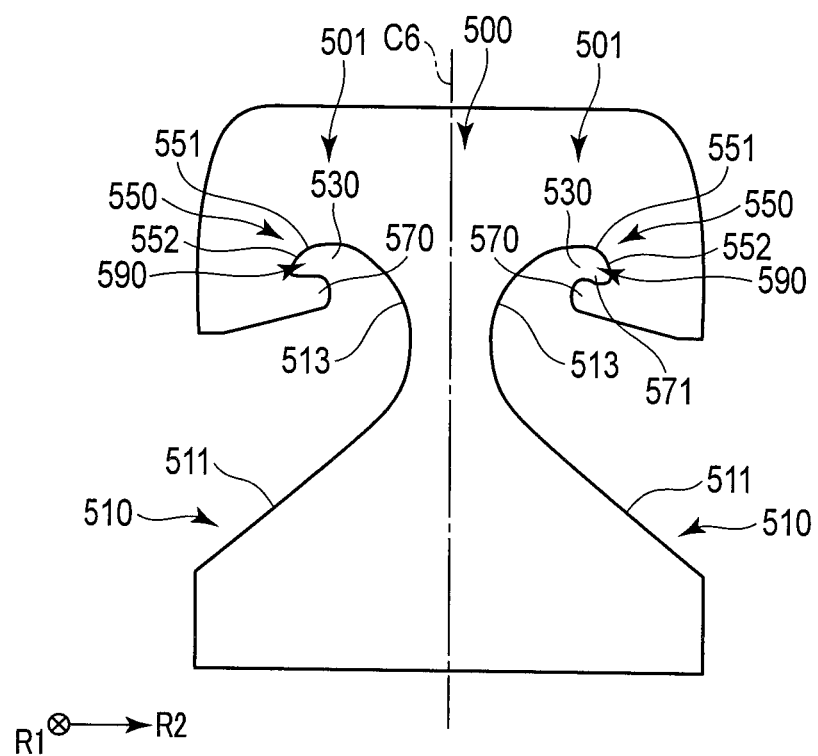
FIG. 5B illustrates how an opening portion and a disengagement preventing portion are modified.

As shown in FIG. 5B, the opening portion 530 may be narrowed in the introduction direction, i.e., from the second guide portion 513 to the second regulating/fixing portion 552. This structure enables the use of treatment tools 400 having various thicknesses.

[Modification of Disengagement Preventing Portion 570]

As shown in FIG. 5B, the disengagement preventing portion 570 may include a groove portion 571 engageable with the guide member 300. With this structure, the guide member 300 is reliably prevented from dropping off, and the operator feels the held part 307 click and is thereby informed that the held part 307 has been reliably positioned and fixed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion portion configured to be inserted into a lumen;
an operation portion coupled to a proximal end side of the insertion portion;
an opening provided in the operation portion, the opening being formed at a height above a surface of the operation portion in a central axis direction of the opening, the opening being in communication with the lumen; and
a holding mechanism configured to hold a guide wire inserted into the opening such that an exposed portion of the guide wire located outside the opening is bent relative to a central axis of the opening,
wherein the holding mechanism comprises:
a first holder comprising:
a first guide surface;
a second guide surface;
a first regulating/fixing surface; and
a first disengagement preventing surface;
wherein the first guide surface being configured to guide the guide wire at the exposed portion located outside the opening to the second guide surface, the second guide surface being configured to pass the guide wire guided by the first guide surface to the first regulating/fixing surface, the first regulating/fixing surface being continuous with the second guide surface and configured to fix the guide wire passing through the second guide surface at a first height in the central axis direction equal to or lower than the height of the opening, the first disengagement preventing surface being continuous with the first regulating/fixing surface and being configured to prevent the guide wire from being removed from the first regulating/fixing surface portion; and
a second holder comprising:
a third guide surface;
a fourth guide surface;
a second regulating/fixing surface; and
a second disengagement preventing surface;
wherein the third guide surface being configured to guide the guide wire at the exposed portion located outside the opening to the fourth guide surface, the fourth guide surface being configured to pass the guide wire guided by the third guide surface to the second regulating/fixing surface, the second regulating/fixing surface being continuous with the fourth guide surface and configured to fix the guide wire passing through the fourth guide surface at a second height in the central axis direction equal to or lower than the height of the opening, the second disengagement preventing surface being continuous with the second regulating/fixing surface and being configured to prevent the guide wire from being removed from the second regulating/fixing surface; and wherein the first guide surface is not continuous with the third guide surface.

2. The endoscope according to claim 1, wherein one or more of the first and second regulating/fixing surfaces are configured to fix the guide wire, with a tension applied to the guide wire member, such that a positioning and fixing state can be maintained even if a treatment tool inserted over the guide wire and into the lumen moves.

3. The endoscope according to claim 2, wherein one or more of the first and second regulating/fixing surfaces comprise:
a first portion which prevents the guide wire inserted into the first and second regulating/fixing surfaces from moving in the central axis direction of the holding mechanism; and
a second portion arranged perpendicular to a flat face where the opening is arranged and which prevents the guide wire from moving in a perpendicular direction perpendicular to the central axis direction of the holding mechanism.

4. The endoscope according to claim 1, wherein one or more of the second and fourth guide surfaces are at a third height equal to or lower than the height of the opening, and
one or more of the first and third guide surfaces are slanted with reference to a flat face where the opening is arranged such that the first and third guide surfaces are at a position lower than the height of the opening.

5. The endoscope according to claim 1, wherein one or more of the first and second disengagement preventing surfaces are parallel to a flat face where the opening is arranged.

6. The endoscope according to claim 5, wherein one or more of the first and second disengagement preventing surfaces are opposed to part of the first and second regulating/fixing surfaces, respectively, and are away from the first and second regulating/fixing surfaces, respectively, by a distance corresponding to a diameter of the guide wire.

7. The endoscope according to claim 5, wherein the holding mechanism is arranged on a straight line connecting the opening and a side region of the operation portion, such that the guide wire can linearly extend from the opening to the side region of the operation portion.

8. The endoscope according to claim 7, wherein:
the second guide surface, the first regulating/fixing surface, and the first disengagement preventing surface define a structure which extends away from the first guide surface and is then directed toward the first guide surface such that the guide wire can linearly extend from the opening to the side region of the operation portion; and
the fourth guide surface, the second regulating/fixing surface, and the second disengagement preventing surface define a structure which extends away from the third guide surface and is then directed toward the third guide surface, such that the guide wire can linearly extend from the opening to the side region of the operation portion.

9. The endoscope according to claim 1, wherein the holding mechanism is arranged adjacent to the opening.

10. The endoscope according to claim 9, wherein the holding mechanism is provided in the operation portion, or in a forceps plug portion which is provided in the operation portion.

11. The endoscope according to claim 1, wherein the holding mechanism is integral with or separate from the operation portion, or is integral with or separate from a forceps plug portion which is provided in the operation portion.

12. The endoscope according to claim 1, wherein the first and second regulating/fixing surfaces are arranged parallel to a flat face where the opening is provided.

13. The endoscope according to claim 1, further comprising a wall separating the first and second holders.

14. The endoscope according to claim 13, wherein the wall has a greater thickness between the first and third guide surfaces than between the second and fourth guide surfaces.

15. The endoscope according to claim 1, wherein the first and third guide portions taper outward in the proximal direction along a longitudinal axis of the operation portion.

16. The endoscope according to claim 1, wherein the first and second regulating/fixing surfaces are each a concavity.

17. The endoscope according to claim 1, wherein the first and second disengagement preventing surfaces are each a convexity.

18. The endoscope according to claim 1, wherein the first height is equal to the second height.

19. An endoscope system comprising:
the endoscope according to claim 1; and
the guide wire configured to be inserted into the opening, and configured to guide a treatment tool along the guide wire,
wherein the guide wire is bent from the central axis direction of the opening to a perpendicular direction perpendicular to the central axis direction, and bends toward a side region of the operation portion, and
the guide wire is brought into pressure contact with an inner circumferential face and an inner circumferential edge of the opening, from the opening toward the operation portion, and is brought into pressure contact with a flat face where the opening is arranged, from an upper end of the opening to the flat face, whereby the guide wire is positioned and fixed.

\* \* \* \* \*